United States Patent
Giori et al.

(10) Patent No.: US 8,118,797 B2
(45) Date of Patent: Feb. 21, 2012

(54) FLUSHABLE BODY WASTE COLLECTION POUCHES, POUCH-IN POUCH APPLIANCES USING THE SAME, AND METHODS PERTAINING THERETO

(75) Inventors: Claudio Giori, Riverwoods, IL (US); Bettakeri S. Udayakumar, Darien, IL (US); Ole Pedersen, Brøndby (DK)

(73) Assignee: Hollister Incorporated, Libertyville, IL (US)

( * ) Notice: Subject to any disclaimer, the term of this patent is extended or adjusted under 35 U.S.C. 154(b) by 737 days.

(21) Appl. No.: 12/095,298

(22) PCT Filed: Nov. 21, 2006

(86) PCT No.: PCT/US2006/061164
§ 371 (c)(1),
(2), (4) Date: Jul. 14, 2008

(87) PCT Pub. No.: WO2007/079290
PCT Pub. Date: Jul. 12, 2007

(65) Prior Publication Data
US 2008/0294129 A1    Nov. 27, 2008

Related U.S. Application Data

(60) Provisional application No. 60/740,181, filed on Nov. 28, 2005.

(51) Int. Cl.
*A61F 5/44* (2006.01)
(52) U.S. Cl. .................. 604/332; 604/322
(58) Field of Classification Search .............. 604/322, 604/327, 332, 333, 337–339, 342
See application file for complete search history.

(56) References Cited

U.S. PATENT DOCUMENTS

| | | | |
|---|---|---|---|
| 2,778,362 A | 1/1957 | Pollack | 604/345 |
| 3,089,493 A | 5/1963 | Galindo | 604/342 |
| 3,902,496 A | 9/1975 | Eakin | 604/334 |
| 4,372,311 A | 2/1983 | Potts | 604/364 |
| 4,734,941 A | 4/1988 | DeWitt et al. | |
| 4,762,738 A | 8/1988 | Keyes et al. | 428/34.3 |
| 4,772,279 A | 9/1988 | Brooks et al. | 604/339 |
| 4,826,493 A | 5/1989 | Martini et al. | 604/327 |
| 4,826,495 A | 5/1989 | Petersen | 604/333 |

(Continued)

FOREIGN PATENT DOCUMENTS
EP    0 272 816 A2    6/1988

(Continued)

OTHER PUBLICATIONS

European Examination Report for Application No. 06849133.1-1219, dated Jan. 11, 2011.

(Continued)

*Primary Examiner* — Melanie Hand
(74) *Attorney, Agent, or Firm* — Marshall, Gerstein & Borun LLP

(57) ABSTRACT

A flushable biodegradable pouch having water-dispersible fibers along at least a portion of the outer surface of the pouch's cover layer provided with a water-soluble hydrophilic coating. The pouch's cover layer is water-disintegratable, and the water-soluble hydrophilic coating is a lubricating agent capable of becoming slippery when exposed to water and, upon subsequent drying, again becoming water-soluble upon re-exposure to water. As such, the hydrophilic coating serves as a rewettable, redesolving lubricating agent.

51 Claims, 13 Drawing Sheets

U.S. PATENT DOCUMENTS

| | | | |
|---|---|---|---|
| 4,830,187 A | 5/1989 | Keyes et al. | 206/524.7 |
| 4,868,024 A | 9/1989 | Cross et al. | |
| 4,906,495 A | 3/1990 | Martini et al. | 428/36.7 |
| 4,946,720 A | 8/1990 | Oishi et al. | 428/35.4 |
| 5,009,648 A | 4/1991 | Aronoff et al. | 604/332 |
| 5,108,382 A | 4/1992 | Wright et al. | 604/342 |
| 5,108,807 A | 4/1992 | Tucker | 428/35.2 |
| 5,110,390 A | 5/1992 | Martini et al. | 156/244.11 |
| 5,227,415 A | 7/1993 | Masuda et al. | 524/17 |
| 5,254,607 A | 10/1993 | McBride et al. | 524/52 |
| 5,407,979 A | 4/1995 | Wu et al. | 524/47 |
| 5,417,677 A | 5/1995 | Schneider et al. | 604/332 |
| 5,468,526 A | 11/1995 | Allen et al. | 428/35.4 |
| 5,591,144 A | 1/1997 | Smith et al. | 604/327 |
| 5,674,578 A | 10/1997 | Giori | 428/35.4 |
| 5,691,015 A | 11/1997 | Tsukamoto et al. | 428/35.2 |
| 5,753,782 A | 5/1998 | Hammond et al. | 525/450 |
| 5,769,831 A | 6/1998 | Freeman et al. | 604/332 |
| 5,776,120 A | 7/1998 | Shelley et al. | 604/339 |
| 5,785,695 A | 7/1998 | Sato et al. | 604/339 |
| 5,821,286 A | 10/1998 | Xu et al. | 524/47 |
| 5,865,819 A * | 2/1999 | Cisko et al. | 604/339 |
| 5,912,059 A | 6/1999 | Jones et al. | 428/35.2 |
| 5,938,647 A | 8/1999 | Smith | 604/332 |
| 5,989,235 A | 11/1999 | Quacquarella et al. | 604/332 |
| 6,075,118 A | 6/2000 | Wang et al. | 528/354 |
| 6,127,512 A | 10/2000 | Asrar et al. | 528/272 |
| 6,217,562 B1 | 4/2001 | Brown et al. | 604/327 |
| 6,514,602 B1 | 2/2003 | Zhao et al. | 428/212 |
| 6,552,162 B1 | 4/2003 | Wang et al. | 528/354 |
| 6,766,817 B2 | 7/2004 | da Silva | |
| 6,918,404 B2 | 7/2005 | da Silva | |
| 7,066,586 B2 | 6/2006 | da Silva | |
| 2002/0064614 A1 | 5/2002 | Turnbull | 428/35.4 |
| 2004/0059306 A1 | 3/2004 | Tsal et al. | 604/332 |
| 2005/0084634 A1 | 4/2005 | Giori | |
| 2005/0113770 A1 | 5/2005 | Pedersen et al. | |

FOREIGN PATENT DOCUMENTS

| | | |
|---|---|---|
| EP | 0 320 895 | 6/1989 |
| EP | 0 344 118 | 11/1989 |
| EP | 0 443 728 | 8/1991 |
| EP | 0 611 123 | 8/1994 |
| EP | 0 703 762 | 4/1996 |
| EP | 0 726 068 | 8/1996 |
| EP | 0 833 596 | 4/1998 |
| EP | 0 875 220 A1 | 11/1998 |
| EP | 1 022 127 | 7/2000 |
| EP | 1 557 145 A2 | 7/2005 |
| GB | 2083762 | 3/1982 |
| GB | 2 227 668 | 8/1990 |
| GB | 2 290 713 A | 1/1996 |
| GB | 2 333 462 A | 7/1999 |
| GB | 2 434 316 A | 7/2007 |
| JP | 2004-097699 A | 4/2004 |
| WO | WO 94/28061 | 12/1994 |
| WO | WO 01/82846 | 11/2001 |
| WO | WO-2005/041827 | 5/2005 |
| WO | WO-2005/041828 | 5/2005 |
| WO | WO 2005041827 A2 * | 5/2005 |

OTHER PUBLICATIONS

Office Action for Australian Application No. 2006332603, dated Jan. 25, 2011.

International Search Report for International Application No. PCT/US2006/061164, dated Jun. 12, 2008.

Written Opinion for International Application No. PCT/US2006/061164, dated Jun. 12, 2008.

* cited by examiner

FLUSHABLE BODY WASTE COLLECTION POUCHES, POUCH-IN POUCH APPLIANCES USING THE SAME, AND METHODS PERTAINING THERETO

REFERENCE TO RELATED APPLICATIONS

This is the United States National Phase of international application no. PCT/US2006/061164, having an international filing date of Nov. 21, 2006, and claims priority to U.S. Provisional Application No. 60/740,181, filed Nov. 28, 2005, the entire disclosure of which (including annexes thereto) is incorporated herein by reference.

BACKGROUND AND SUMMARY

Giori Published Patent Application US 2005/0084634 (also published as WO 2005/041827) discloses a biodegradable and toilet-flushable body waste collection pouch, and an appliance and method in which such a pouch constitutes the inner pouch of a peelably separable pouch-in-pouch system. The walls of the inner pouch are composed of an ultra-thin, heat-sealable film impermeable to body wastes comprising a plasticized biodegradable polyester or copolyester externally covered by a soft and water-disintegratable cover layer of biodegradable and water-dispersible fibers. The cover layer and film are weakly bonded together in such a way as to avoid pinholes in the film that might otherwise be caused by the fibers. When used as the inner pouch of a pouch-in-pouch system, the film of the outer pouch is selected to have a melting temperature higher than that of the inner pouch film, with the result that a peripheral heat seal joining the walls of the two pouches together will allow the walls of the outer pouch to be peeled away without delaminating the film and cover layers of the inner pouch.

Pedersen et al Published Patent Application US 2005/0113770 (also published as WO 2005/041828) discloses an ostomy appliance having a face plate assembly and inner and outer pouches joined thereto. The outer pouch is provided with one or more peripherally-extending sealing seams that allow the walls of the outer pouch to be separated by peeling forces applied in directions transverse to such seam or seams. In preferred embodiments, the sealing seams also peelably join the peripheral edges of the outer pouch to those of the inner pouch. A method of disposing of the pouch assembly of such an ostomy appliance is also disclosed.

The disclosures of these aforementioned published applications US2005/0084634 and US 2005/0113770 are fully incorporated in this application by reference.

It has now been found that the flushability of a biodegradable pouch as disclosed in these published applications, and the passage of such a pouch through a sewer system, are greatly enhanced if the water-dispersible fibers along at least a portion of the outer surface of the pouch's cover layer (which is preferably formed of a nonwoven material, particularly a water-disintegratable paper such as cellulosic toilet tissue) are provided with a hydrophilic coating. The coating does not impair the peelability of the seals of a pouch-in-pouch system or interfere with the water dispersibility of the fibers, and is found to be advantageous because it reduces the friction between the outer surface of the pouch and the walls of a flush toilet and passages of a sanitary sewer system. While the coating would normally be applied and dried during production of such a pouch or pouch assembly, or during the tissue paper-film manufacture, it is contemplated that alternatively such a coating might be applied by a user, as by spraying, just prior to discarding the pouch and its contents into a flush toilet.

When applied in production, the coating in the form of a water-based hydrophilic solution is sprayed, rolled, or otherwise applied to the surface of the pouch's tissue cover layer. It is then dried by any suitable means, as in a convection oven. When the pouch is later discarded into the water of a flush toilet, the coating absorbs water and reactivates a hydrophilic film that makes the surface of the pouch slippery, significantly reducing the friction between the pouch and the walls of the toilet and sewer passages. This reduced surface friction has a positive impact on the flush performance of the pouch.

The biodegradable coating contains one or more lubricating agents. One preferred gelling agent is hydroxyethylcellulose, available under the commercial name "Natrosol" from Aqualon, but other lubricating agents considered suitable are hydroxypropylcellulose, carboxymethylcellulose and their salts, guar gums, gelatin, pectin, polyethylene glycol, polyethyleneoxide, polyacrylamides, acrylic acid polymers and their salts, and water-soluble silicone gelling agents. Of particular importance is that such a lubricating agent, after drying following initial exposure to water, must be capable of again becoming water soluble and slippery when re-exposed to water. Thus, it has been found that polyvinyl alcohol is unsuitable as a gelling agent for use in this invention because although it becomes slippery upon initial hydration, once it has dried it is no longer water-soluble. A lubricating agent for use in this invention must be capable of rewetting/redesolving to avoid the risk that the drying of the coating might cause a pouch to stick to the wall of a sewer pipe and not readily release when water is again flushed through the pipe.

In addition to a lubricating agent or agents, the coating material may include preservatives, surfactants, thickeners, pH buffers, slip agents, odor neutralizers, deodorants and other additives. Examples of thickeners include, but are not limited to, carbomers, gums, poloxamers, gelatin, pectin and nonionic, zwitterionic and ionic gel formers.

By way of example, a coating solution of 2% hydroxyethylcellulose (Natrosol) and 0.3% Phenonip (a commercial mixture of preservatives containing phenoxyethanol, methylparaben, ethylparaben, propylparaben butylparaben and isobutylparaben) may be applied to the paper tissue layer (25 g Shawano cellulosic tissue code 3040 from Shawano Specialty Papers) of a waste collection pouch as disclosed in the aforementioned published applications, the disclosures of which are incorporated herein by reference. The coating is then dried by placing the pouch in a convection oven at 75° C. for approximately one hour. Drying may also be achieved by using infrared lamps, heating elements or other sources of heat, and may be boosted by negative pressure and air circulation.

The desired load of coating may be achieved in single or multiple applications.

It has been found that an inner pouch of the type disclosed the aforementioned published applications, formed of an ultra thin biodegradable film with a tissue covering layer but without the hydrophilic coating described herein, may be safely flushed through a toilet with a pouch load of up to about 110 g, whereas if the tissue layer of a similar pouch is provided with the hydrophilic coating of this invention, the pouch load may be safely and effectively increased to 150 g.

DETAILED DESCRIPTION

Figure 1:
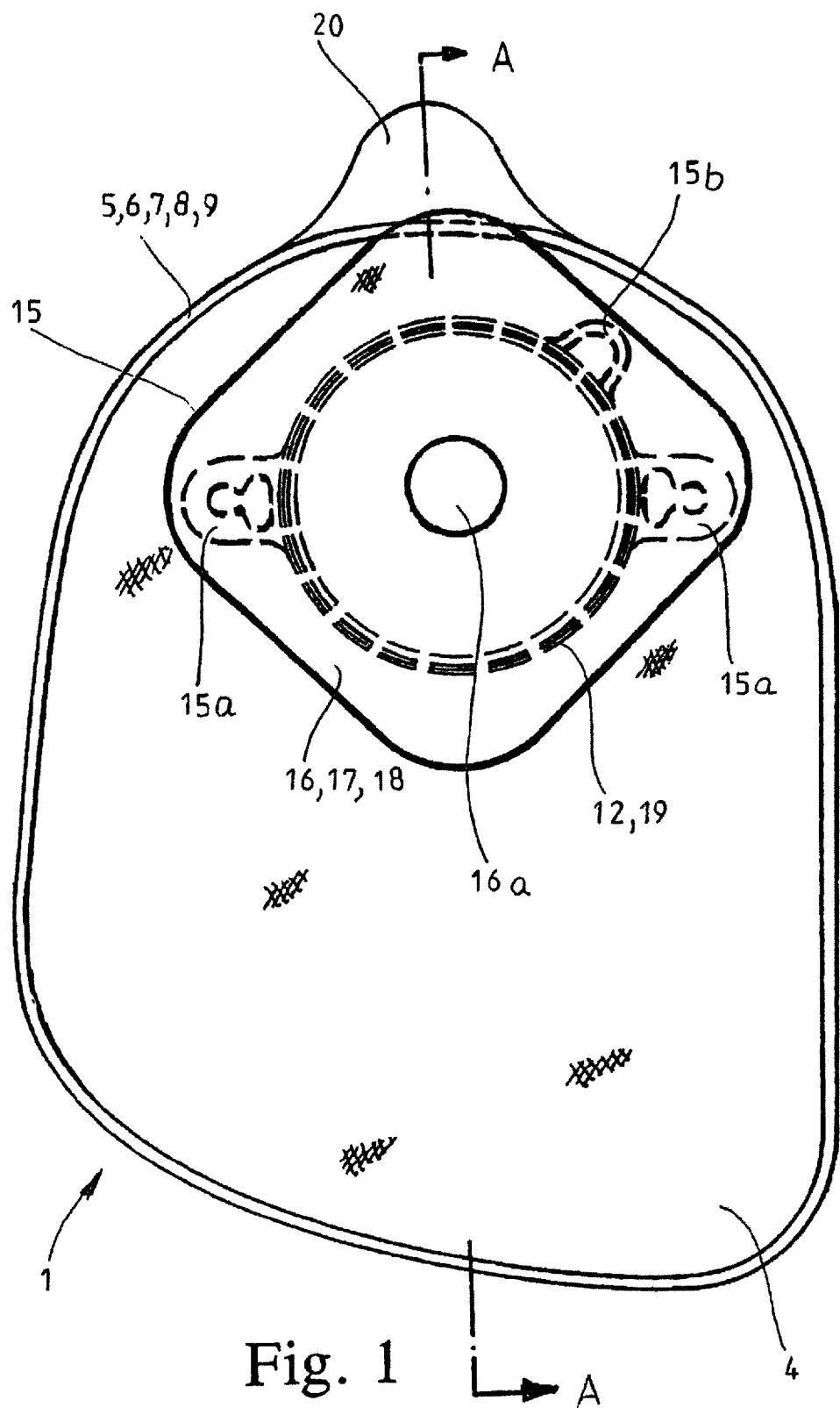
FIG. 1 is a schematic plan view, seen from the body side, of a first embodiment of a two-piece ostomy pouch according to the invention.
Figure 2:
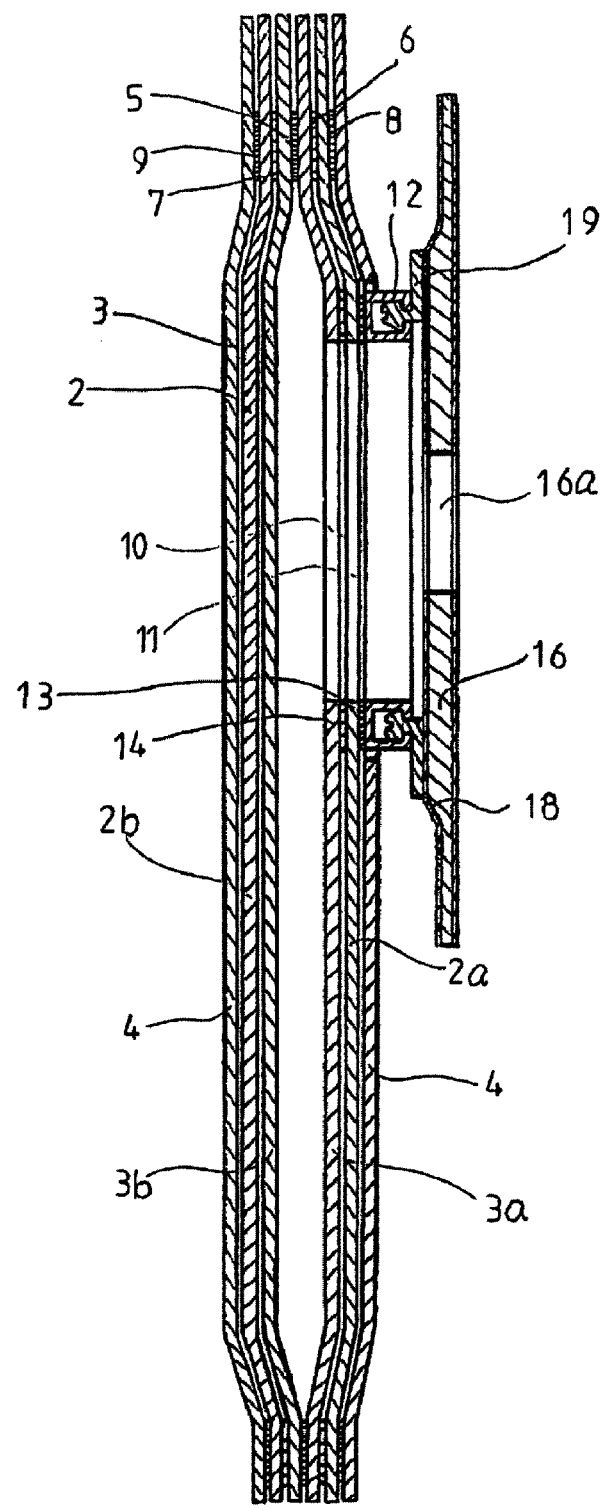
FIG. 2 is a diagrammatic cross sectional view taken along line A-A in FIG. 1 with the film thicknesses exaggerated for illustrative purposes.
Figure 3:
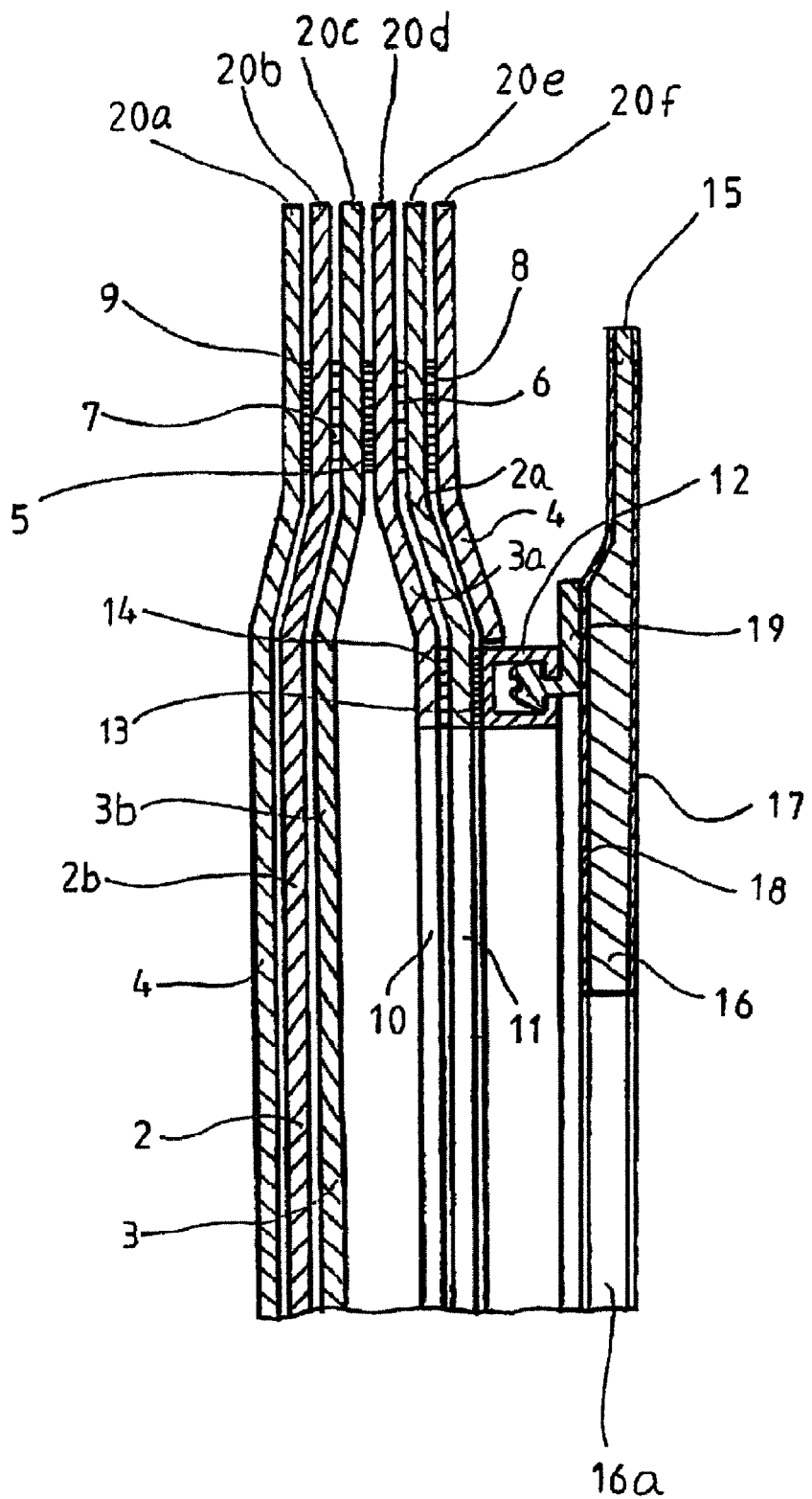
FIG. 3 is an enlarged scale view of the top portion of FIG. 2.

Referring now to FIGS. 1-3, an ostomy appliance referenced generally by the numeral 1 comprises an outer pouch 2 comprised of a body side or proximal wall 2a and an opposed distal wall 2b. The appliance furthermore comprises an inner pouch 3 comprised of a proximal wall 3a and a distal wall 3b. The outer pouch walls 2a and 2b are covered by a comfort layer 4 of a non-woven material.

The walls 2a and 2b are made of a flexible plastic film that is impermeable to liquids, gasses and odors. The walls 3a and 3b are made of a flexible plastic film that is impermeable to liquids and gasses and permeable to odors.

The inner pouch 3 is formed by sealingly securing the two inner walls 3a and 3b to each other along the peripheries thereof by means of an inner pouch seam 5 either being a heat sealing seam or an adhesive seam.

The outer pouch 2 is formed by sealing the proximal and distal outer pouch walls 2a and 2b, respectively, to the inner pouch proximal and distal walls 3a and 3b, respectively by means of peelable sealing seams 6 and 7, respectively, extending along the outer periphery of the outer and inner pouch walls.

The comfort layers 4, which are optional, are sealed to the outer pouch walls 3a and 3b by means of heat sealing or adhesive seams 8 and 9, respectively, extending along the outer periphery of the outer pouch walls.

Both the inner pouch 3 and the outer pouch 2 have a stoma receiving aperture 10 and 11, respectively in the proximal walls 3a and 2a, respectively.

The appliance 1 further comprises a pouch coupling ring 12 secured to the proximal outer pouch wall 2a by means of a circumferential heat seal 13 or other suitable means. The area surrounding the aperture 10 of the proximal inner pouch wall 3a is attached to the corresponding area of the proximal outer pouch wall 2a by means of an annular peelable seam 14.

The appliance 1 further comprises a face plate assembly 15 having an adhesive layer 16 for adhering the face plate assembly to the peristomal surface of a user of the appliance 1 after having removed a release sheet 17 covering the proximal or body side surface of the adhesive layer 16. The adhesive layer is provided with a stoma receiving aperture 16a.

A carrier sheet 18 is attached to the distal surface of the adhesive layer 16, and a face plate coupling ring 19 is secured to the carrier sheet 18, such that interconnection of the two coupling rings 12 and 19 as shown in FIG. 2 will allow the pouch assembly 2, 3 to be adhered to the peristomal skin surface of a user with the stoma inserted in the apertures 16a, 10 and 11 such that stomal discharge may enter the inner pouch 3. The face plate coupling ring 19 is provided with two optional belt loops 15a and an optional burp tab 15b.

Figure 13:
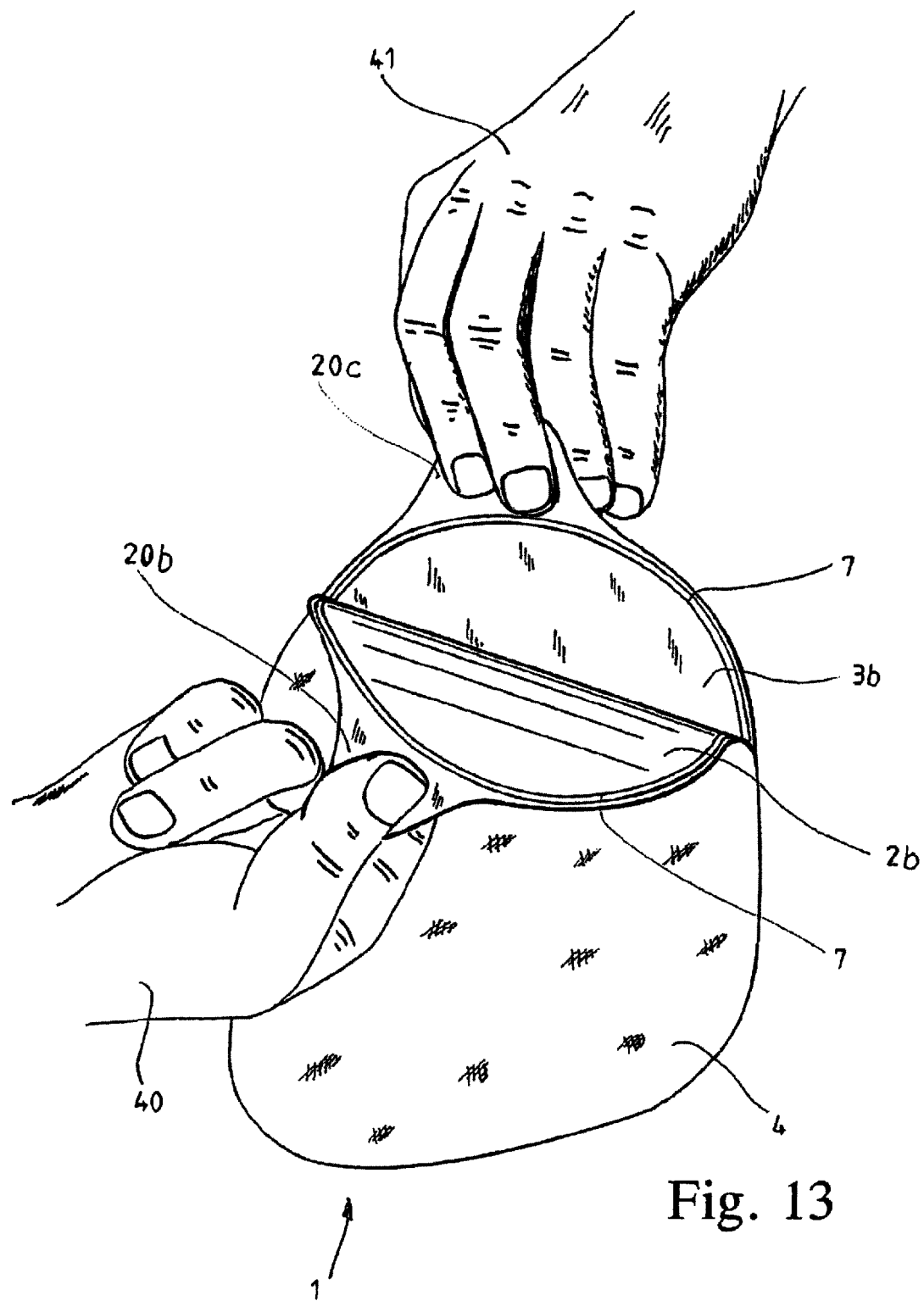
FIG. 13 is a schematic frontal view seen in the direction towards the body of the user of an ostomy appliance according to the invention illustrating the peeling off of the distal outer pouch wall.
Figure 14:
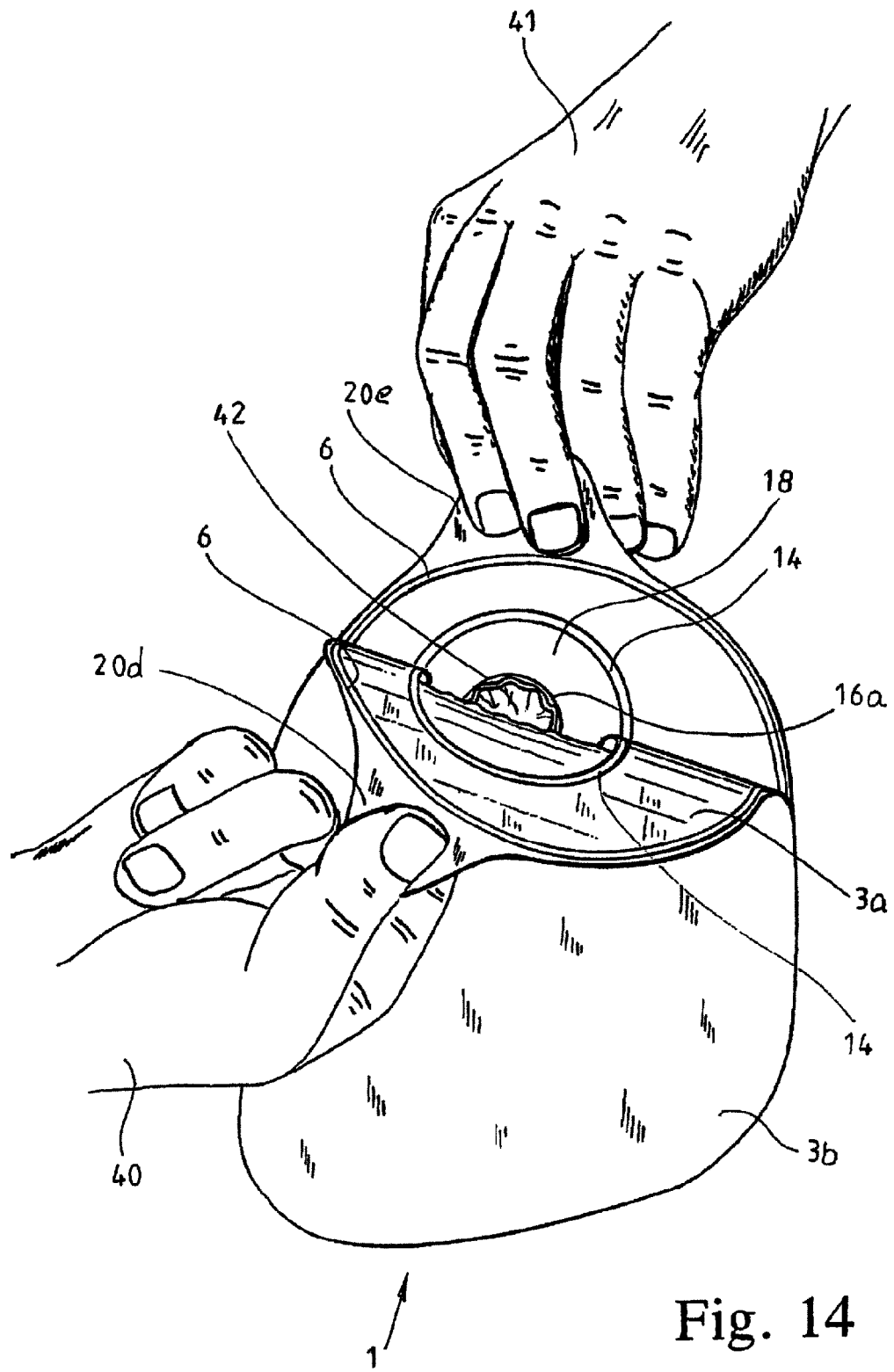
FIG. 14 is a view similar to FIG. 13 illustrating the peeling off of the inner pouch.

The inner and outer walls 2a, 2b, 3a, 3b as well as the comfort layers 4 project outwardly and upwardly are prolonged at the top of the appliance to form a tongue or projection 20 for providing non-connected and separable gripping tabs 20a-20f for the separation of the two pouches for disposal thereof as explained below in connection with FIGS. 13 and 14.

In use, when the inner pouch is full of stomal discharge and the pouch needs to be replaced by an empty pouch, the user or a helper (see FIGS. 3 and 13) grips the tabs 20a and 20b together with one hand 40 and the rest of the tabs with the other hand 41 and pulls the tabs 20a and 20b away from the body and downwardly. Hereby the connection between the outer pouch wall 2b and the inner pouch wall 3b by means of the peelable sealing seam 7 is broken or disrupted such that the proximal outer pouch wall 2b with its comfort layer 4 is peeled away from the appliance 1.

Thereafter, the user (see FIGS. 3 and 14) grips the tabs 20c and 20d together with one hand 40 and the tabs 20e and 20f with the other hand 41 and pulls the tabs 20c and 20d outwardly and downwardly whereby the peelable sealing seam 6 gives way so that the inner pouch 3 is peeled away from the outer pouch proximal wall 2a until the level of the top point of the peelable sealing seam 14 is reached. This peelable seam 14 also gives way to the pulling force exerted on the tabs 20c and 20d so that finally the entire inner pouch 3 with its content of stomal discharge has been peeled away from the proximal outer pouch wall 2a. The stoma 42 of the user is now exposed (see FIG. 14).

Now the inner pouch 3 with contents can be deposited in the bowl of a toilet and flushed away while the proximal outer pouch wall 2a with comfort layer 4 and coupling ring 13 can be removed from the face plate assembly 15. The outer pouch walls 2a and 2b with corresponding comfort layers 4 and the coupling ring can now be folded together and be disposed of in some other manner, for instance in a pocket, a hand bag or a refuse container.

The material of the inner and outer pouch walls may be a film of any suitable plastic material. The outer pouch wall film material is impermeable to liquids, gasses, while the inner pouch wall film is impermeable to liquids and gasses, but not necessarily to odors. By allowing the inner pouch wall film to be permeable to odors, the film may be made thinner and thus be more easily disintegrated and biodegraded.

It is preferable that the inner pouch wall film material be biodegradable so that the sewage treatment facilities are not inconvenienced to an unnecessary degree. By allowing the inner pouch wall film to be permeable to odors, the film may be made thinner and thus be more easily disintegrated and biodegraded.

Examples of biodegradable films suitable for the inner pouch walls 3a and 3b are biodegradable aliphatic polyesters such as polycaptrolactone.

A biodegradable and liquid impermeable material that currently is considered suitable for the inner pouch wall film are biodegradable aliphatic polyesters such as polycaprolactone (for instance TONE Polymer supplied by Dow Chemical Company) or a biodegradable aliphatic-aromatic copolyester (for instance ECOFLEX supplied by BASF).

The peelable sealing seams 6, 7 and 14 may be provided in various ways, for instance by utilizing a peel lacquer or varnish which gives a peelable adhesion to either the inner or the outer pouch walls or to both walls. The type of peelable lacquer or varnish depends on the material chosen for the pouch bag films.

Peel lacquers that currently are considered to be suitable for certain film materials are "Appeel" resins from the company duPont, and hot melt peelable adhesives supplied under the trade names Dispomelt 34-2881, 34-5519, Instaweld 34-3306 and Bondmaster 34-3306 by the companies National Starch Adhesive and Chemical Corporation.

Another way of implementing the peelable sealing seams is to use an intermediate film of polybutylene or an intermediate three-layer film supplied by the company Rexam under the trade name Core-Seal, the peeling occurring between the two outer films and the internal film or layer, the external films being securely heat sealed to the inner and outer pouch wall films.

A further way of implementing the peelable seams is to use a silicone release film such as the type used for labels.

In the context of the present invention, the term peelable utilised in the specification and claims is to be understood to mean that the connection between two films, be it by means of an adhesive, heat sealing or other means, can be broken, disrupted or eliminated by manually urging one film away from the other without compromising the integrity of the films.

Figure 5:
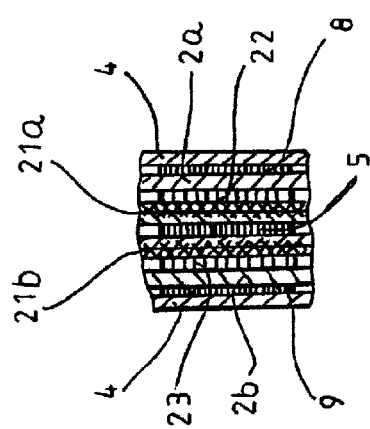
FIG. 5 is an enlarged scale view of the area encircled in FIG. 4.
Figure 4:
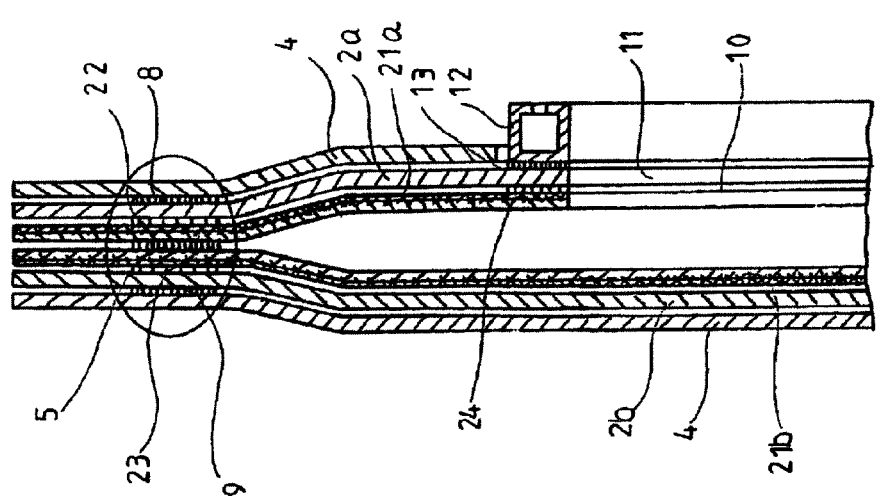
FIG. 4 is a cross sectional view corresponding to FIG. 3 of a second embodiment of the ostomy appliance according to the invention.

A currently preferred manner of providing peelable sealing seams will now be described with reference to FIGS. 4-5. The embodiment of FIGS. 4-5 is identical to the embodiment of FIGS. 1-3 except for the inner pouch bag walls 21a and 21b that are made of a heat sealable, liquid and gas impermeable, odor permeable film of plastic material laminated to a web of paper.

The paper sheet (indicated by cross hatches) is located on the outer surface of the inner pouch walls 21a and 21b facing the outer pouch walls 2a and 2b, respectively.

The peelable sealing seams 22, 23 and 24 between the inner pouch walls 21a, 21b and the outer pouch walls 2a, 2b, respectively are provided by heat sealing whereby the plastic material of the outer pouch walls 2a and 2b melts and flows into the interstices of the paper sheet such that a bond is created between the films 2a and 2b and the paper sheet.

However, as the plastic material does not flow all the way through the paper sheet to fuse with the plastic material of the inner pouch walls 3a and 3b, respectively, the strength of the bond created by the heat sealing is dependent on the internal adherence forces between the fibers of the paper sheet and/or between the fibers and the films 2a, 2b and 3a, 3b.

By applying a peeling force transversely to the surface of the paper sheet, the bond can be broken manually so that the walls 2a and 3a and 2b and 3b can be separated by the manual peeling action described above for separating the outer pouch walls from the inner pouch for toilet disposal of the latter.

Alternatively, the outer pouch walls may be peelably adhered to the paper sheet by means of an adhesive having greater adhesion strength than the inner cohesion of the paper fibers. Finally, it is conceivable that the peelability of the seams be obtained by a relatively weak adhesion between, on the one hand, the outer pouch walls and/or the inner pouch walls and, on the other hand, the paper sheet so that the inner cohesion of the paper fibers is of less importance.

When peeling the peelable seams 8 and 9, the peeling force necessary for disrupting the peelable sealing seams will vary along the seams according to the width of the seam peeling front, i.e. the width of the seam in the direction at right angles to the peeling direction. Thus, the necessary peeling force will be largest when the peeling front is located at the top and bottom of the sealing seams 8 and 9 in for instance FIG. 8 and the necessary peeling force will be smallest when the peeling front of the seams 8 and 9 is located along the sides of the pouch.

The necessary peeling force should be such that the peeling force can easily be exerted by the user of the appliance without risk of ripping the outer pouch walls 2a and 2b and especially the inner pouch walls 3a and 3b when peeling. However, the necessary peeling force should also reflect attachment forces in the peelable seams 8 and 9 sufficient for ensuring the integrity of the appliance during use thereof.

It is currently believed that the necessary peeling force should be in the range of between approx. 0.5 Newton and approx. 6 Newton, preferably between approx. 0.7 Newton and approx. 5.5 Newton, even more preferably between approx. 0.8 Newton and approx. 5.0 Newton, even more preferably between approx. 0.9 Newton and approx. 4.5 Newton and most preferably between approx. 1.0 Newton and approx. 4.0 Newton.

The use of paper as the outer layer of the inner pouch double-layered walls affords further important advantages regarding the strength of the inner pouch, the feel and appearance of the inner pouch and the disposability of the inner pouch by being flushed through a toilet.

Water-disintegratable paper in dry condition has a relatively large tensile strength, and thus laminating paper on to a film of plastic material allows using a thinner film for achieving liquid and gas impermeability as well as sufficient combined strength.

This is advantageous from an economic viewpoint as less relatively expensive plastic material is required for the inner pouch walls.

Furthermore, when paper becomes wet, it loses some of its cohesion and tensile strength, and therefore the disposability of the inner pouch in a toilet is enhanced, as the decomposition of the inner pouch is facilitated because, firstly, the film is thinner and, secondly, because plastic material, even though it is a biodegradable plastic material, is relatively slow to disintegrate and biodegrade.

Finally, the user will be more comfortable throwing something feeling and looking like a paper or toilet tissue bag into the toilet than throwing a plastic bag into the toilet.

Paper types currently considered to be suitable for use in the inner pouch wall laminate are 100% cellulosic tissue paper of low wet strength such as Little Rapids Corp-Shawano Specialty Papers cellulose based paper Grade 3040 supplied by LRC-Shawano Specialty Papers, USA or paper including a binder such as Superseal Teabag Paper grade 478-401 supplied by J.R. Crompton Ltd, UK.

In the context of the present invention, the term paper utilised in the specification and claims is to be understood to mean a non-woven fibrous web containing a substantial amount of cellulose fibers, preferably more than 30% by weight, more preferably more than 50% by weight, even more preferably more than 60% by weight and even more preferably more than 70% by weight, most preferably more than 95% by weight, and preferably without a binder for reasons of biodegradability.

Figure 6:
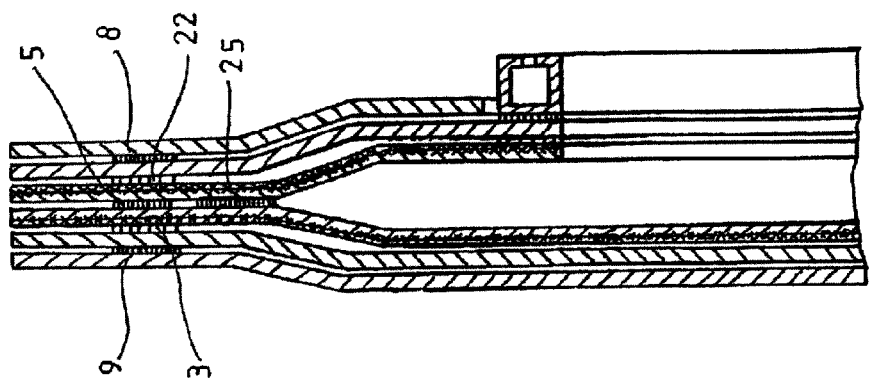
FIG. 6 is a view corresponding to FIG. 4 of a modification of the embodiment of FIGS. 4-5.

Referring now to FIG. 6, the embodiment shown therein is identical to the embodiment of FIGS. 4-5 except for an additional peripheral heat sealing seam 25 of the inner pouch walls 21a and 21b to each other.

The purpose of this additional seam 25 is to safeguard against leakage of stomal discharge from the inner pouch if the peeling of the proximal outer pouch wall 2b from the distal inner pouch wall 21b or the peeling of the proximal inner pouch wall 21a from the proximal outer pouch wall 2a results in ripping of one or both of the inner pouch walls because of too forceful peeling or other reasons. The heat sealing seam 25 is shown spaced from the heat sealing seam 5, but they may be contiguous.

Figure 7:
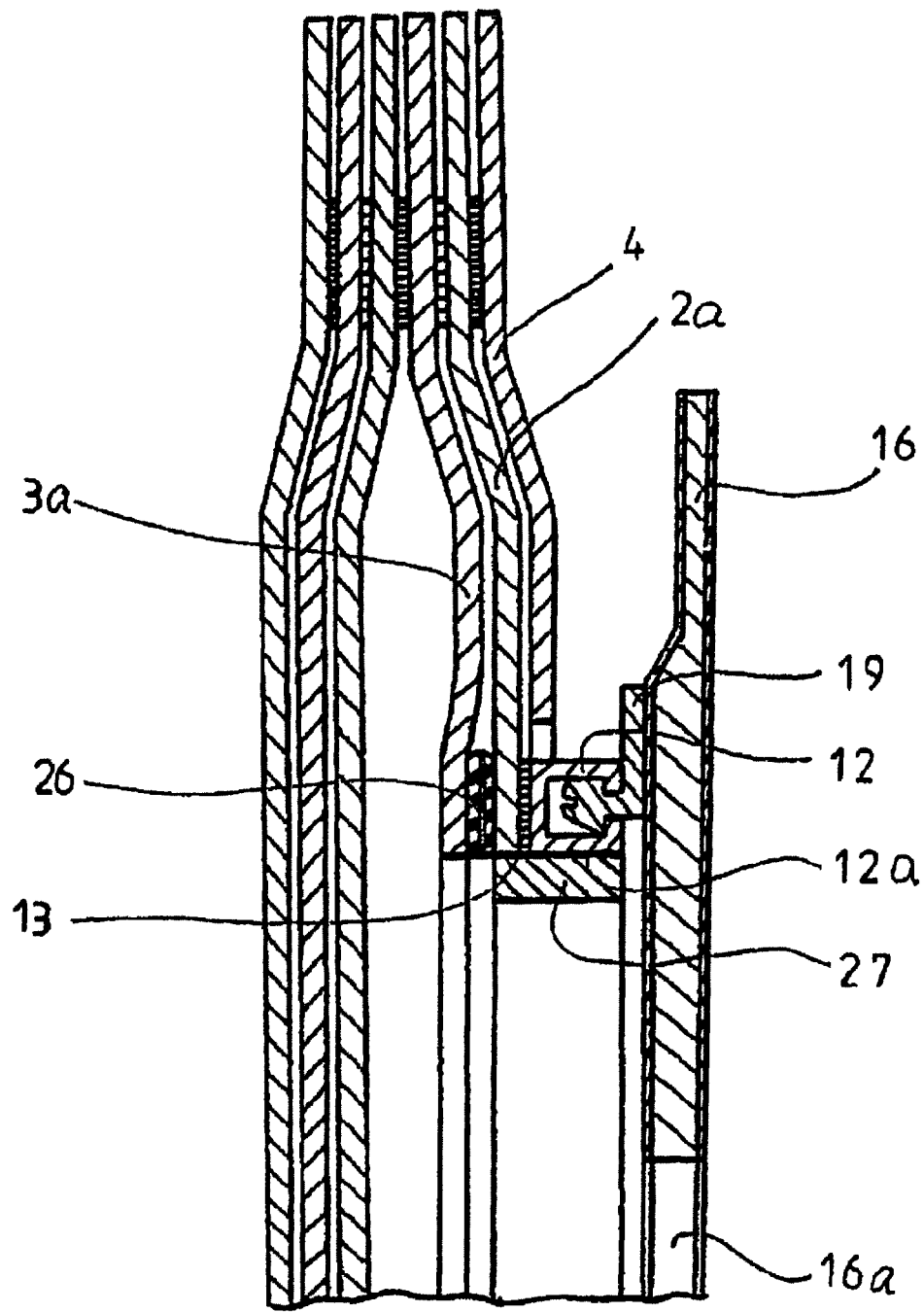
FIG. 7 is a view corresponding to FIG. 4 of a further embodiment of a two-piece ostomy appliance according to the invention.

Referring now to FIG. 7, the embodiment shown therein is identical to the embodiment of FIGS. 1-3 except that the peelable sealing seam 26 corresponding to sealing seam 14 in FIGS. 1-3 is an annular film or textile with adhesive on both surfaces so that it adheres to both the inner pouch wall 3a and the outer pouch wall 2a, and that an annular insert 27 of cardboard is arranged as a tight fit against the inner surface 12a of the coupling ring 12.

The function of the annular insert 27 is to protect the inner surface 12a of the coupling ring 12 from contact with stomal discharge such that when disposing of the inner pouch in a toilet, the insert can be removed (for instance by being pressed out manually) and discarded in the toilet such that no part of the outer pouch and coupling ring is soiled by the stomal discharge and thus can be carried away in a pocket with no risk of bad odors and soiling of the pocket.

Protection of the inner surface of the coupling ring against being soiled by stomal discharge may also be achieved by peelably adhering an outwardly extending collar portion of the inner pouch wall 3a adjacent the coupling ring to said inner surface such that the collar will serve the same purpose as the insert 27, and upon removal of the inner pouch from the coupling ring will leave the coupling ring free of stomal discharge.

The releasable attachment of the pouch assembly comprising the inner pouch 3 and outer pouch 2 to the adhesive face plate assembly by means of the coupling rings 12 and 19 may be substituted by a releasable adhesive attachment of the outer pouch 2 and/or the inner pouch 3 to the carrier sheet 18 either directly or by means of releasable adhesion between an intermediate element attached to the carrier sheet 18 and/or the outer pouch 2 and/or the inner pouch 3 such that a new pouch assembly 2, 3 may be adhered to the face plate assembly 15 after removal and disposal of the previous pouch assembly.

Figure 9:
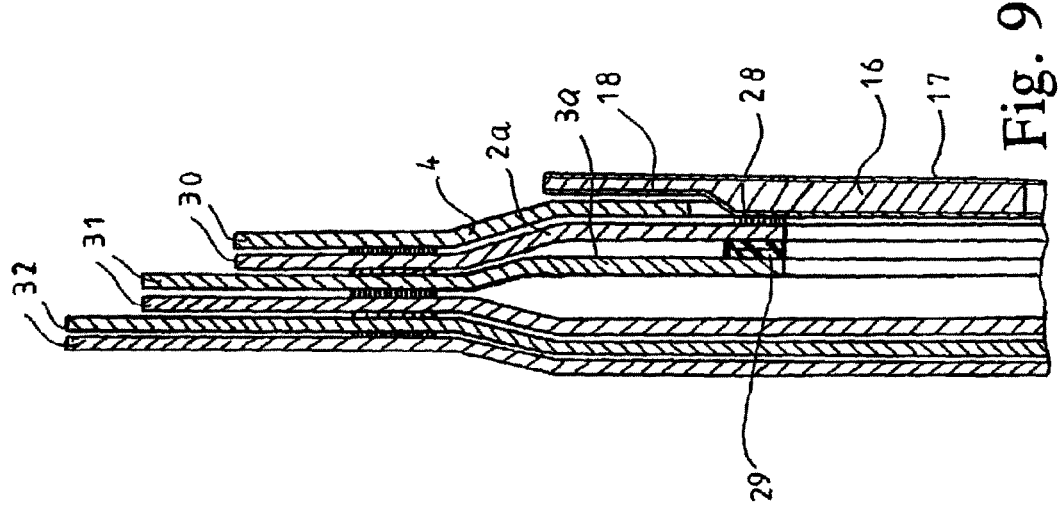
FIG. 9 is a diagrammatic broken away, cross sectional view of the top portion of the appliance of FIG. 8 taken along line B-B in FIG. 8 with the film thicknesses exaggerated for illustrative purposes.
Figure 8:
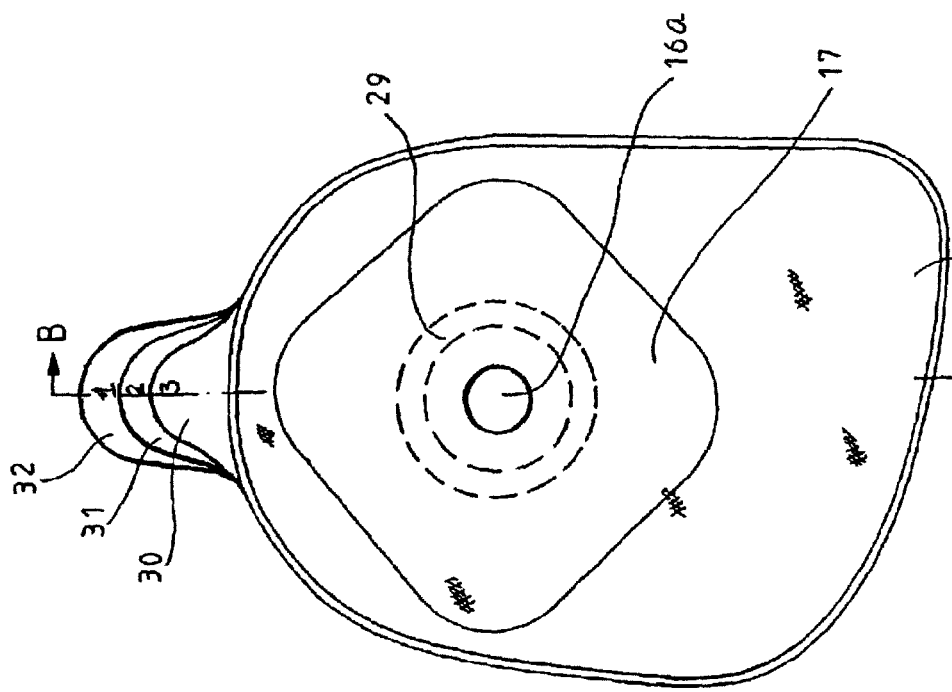
FIG. 8 is a schematic plan view, seen from the body side, of a first embodiment of a one-piece ostomy pouch according to the invention.

Referring now to FIGS. 8-9, a one-piece ostomy appliance is shown, wherein the proximal outer pouch wall 3a is heat sealed to the carrier sheet 18 by means of an annular heat sealing seam 28 while the proximal inner pouch wall 2a is peelably sealed to the outer pouch wall 3a around the stoma receiving aperture by means of a peelable sealing seam 29 constituted by an annular film or textile with adhesive on both of its opposed surfaces.

At the top of the pouch the tongue 20 of the embodiment of FIGS. 1-3 has been substituted by three tongues 30, 31 and 32. The tongues are staggered and marked with the numerals 1, 2 and 3 to indicate the order in which they are to be gripped and pulled away, the tongue 32 being gripped first by one hand while gripping the tongue 31 with the other hand and pulling the tongue 32 away from the body of the user and so on until the desired separation of the appliance into two outer bag walls and the inner pouch has been accomplished.

Figure 10:
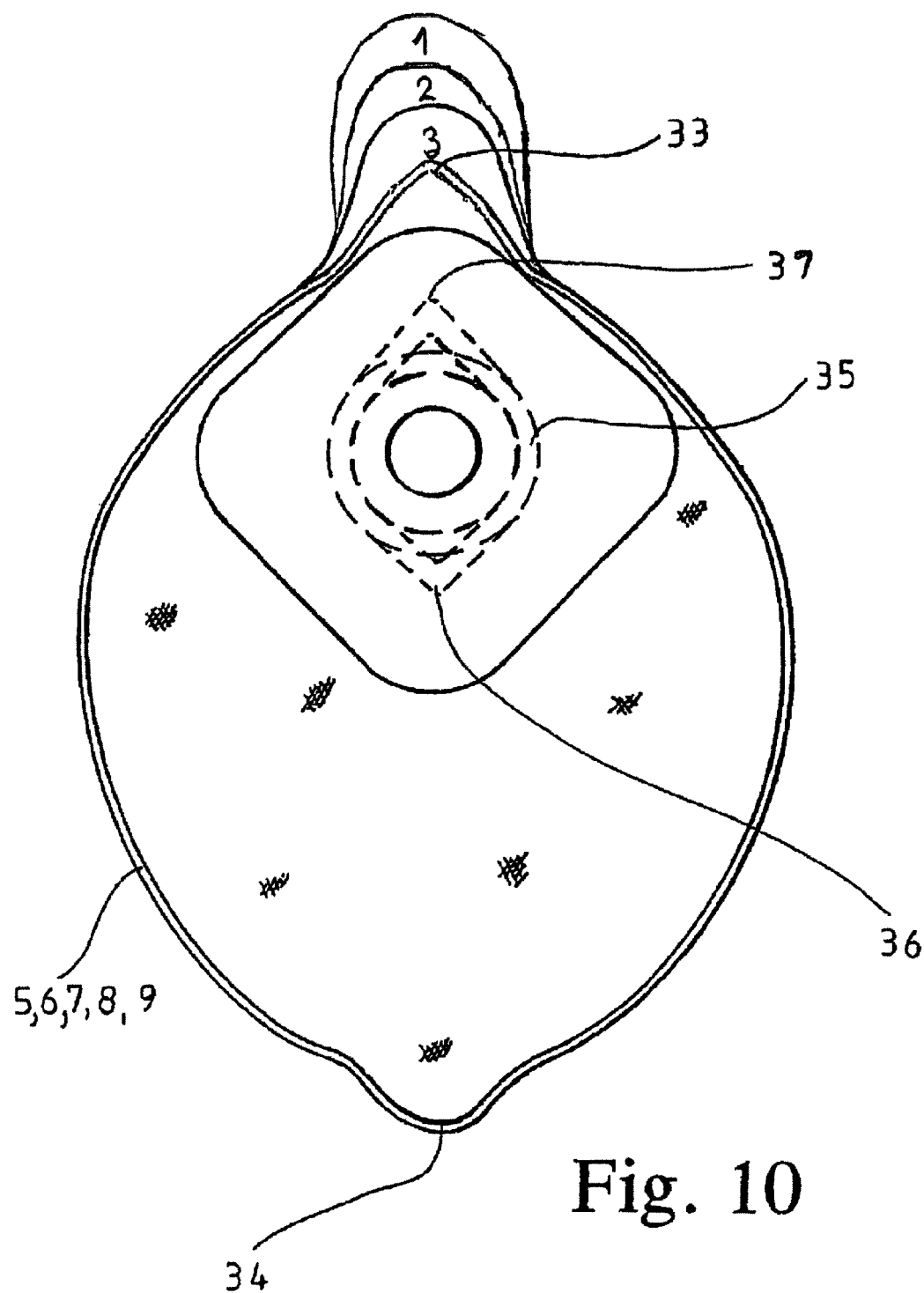
FIG. 10 is a view corresponding to FIG. 8 of a second embodiment of a one-piece ostomy pouch according to the invention.

Referring now to FIG. 10, this embodiment of a one-piece ostomy appliance according to the invention is very similar to the embodiment of FIGS. 8-9, but is provided with a lemon-like contour of the sealing seams 5, 6, 7, 8 and 9.

The object of this pointed contour is to facilitate the peeling separation of the peelable sealing seams 6 and 7 between the outer pouch walls 2a and 2b and the inner pouch walls 3a and 3b, respectively.

The pointed ends 33 and 34 act to concentrate the peeling forces and thus render it easier to initiate and end the peeling operation, respectively by presenting a small attachment area to start and end the peeling action.

The peelable sealing seam 35 between the inner pouch proximal wall and the outer pouch proximal wall around the stoma receiving apertures in these walls can either be round or have pointed ends 36 and 37 for facilitating the initiation and ending of the peeling operation on peelable sealing seam 35.

Figure 11:
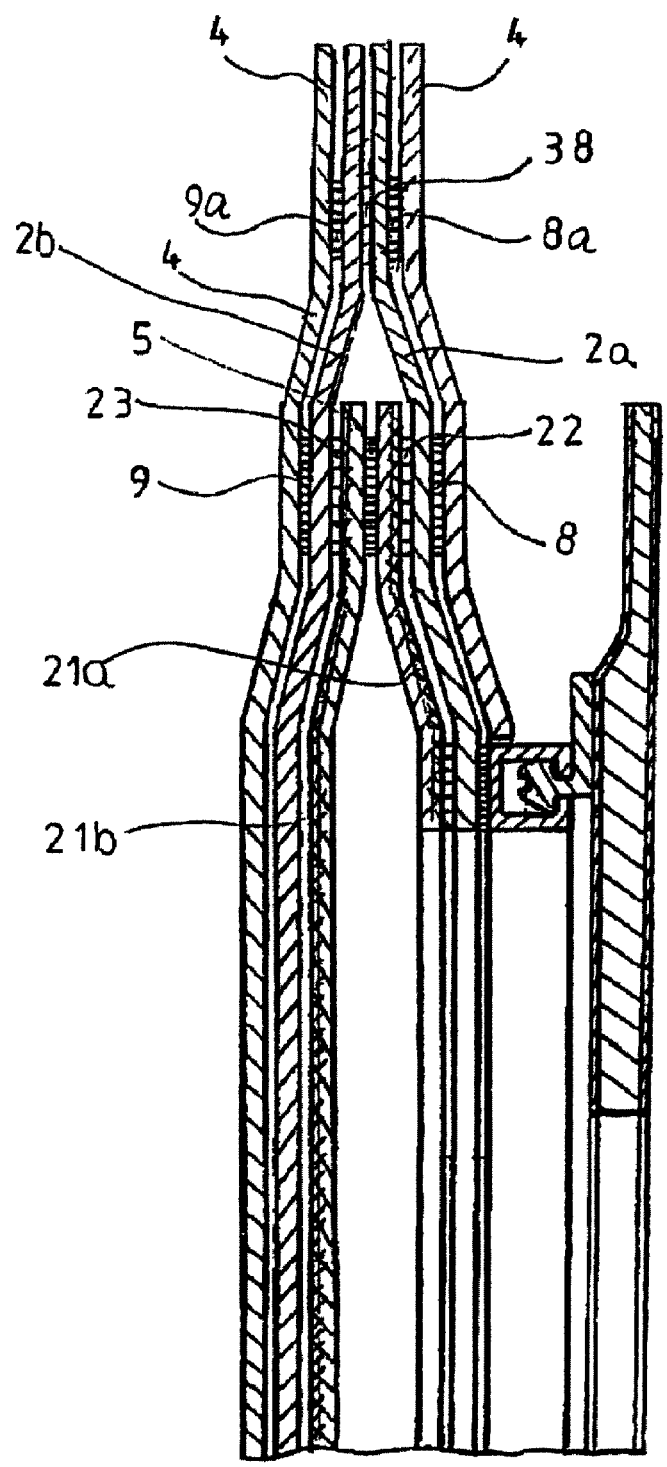
FIG. 11 is a view corresponding to FIG. 4 of a further embodiment of a two-piece ostomy appliance according to the invention.

Referring now to FIG. 11, this embodiment is very similar to the embodiment of FIG. 4 except that the outer pouch film walls 2a and 2b and the comfort layers 4 have been extended beyond the periphery of the inner pouch walls 21a and 21b and an additional peelable sealing seam 38 has been provided for peelably joining the outer pouch walls together as a safety measure in case odors or flatus gasses wick through the fibers of the paper web laminated to the inner pouch film wall. In such case the additional sealing seam 38 will prevent the gasses and odors from exiting the outer pouch. Furthermore, this extra seam 38 will safeguard against water (for instance during showering) penetrating the fibers of the paper layer and reducing the sealing strength of the peelable sealing seems 22 and 23.

Figure 12:
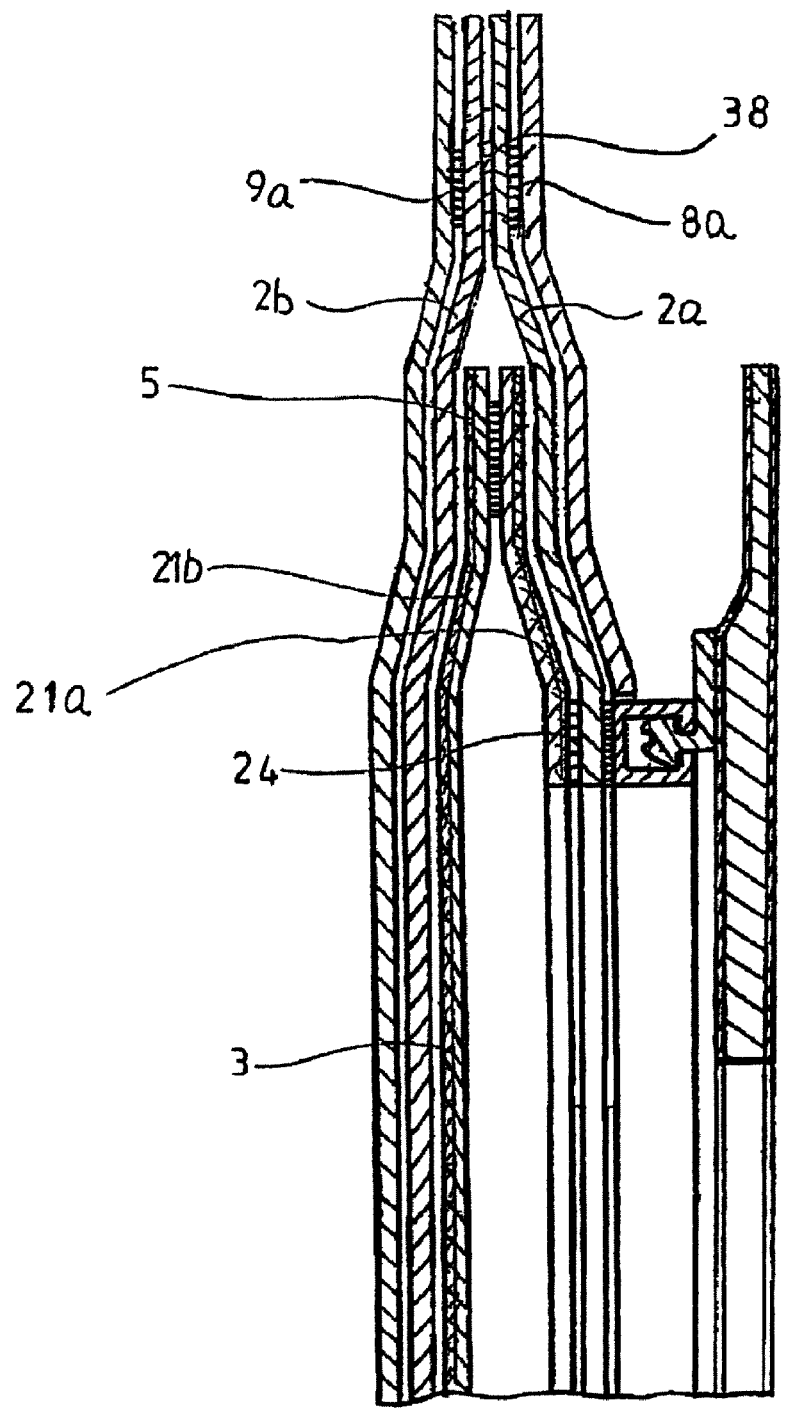
FIG. 12 is a view corresponding to FIG. 4 of a yet further embodiment of a two-piece ostomy appliance according to the invention.

Referring now to FIG. 12, this embodiment is identical to the embodiment of FIG. 11 except that the peelable sealing seams 22 and 23 between the film walls 2a and 21a and 2b and 21b, respectively as well as the sealing seams 8 and 9 between the comfort layers and the film walls 2a and 2b, respectively, have been left out so that the inner pouch is only connected to the outer pouch by the peelable sealing seam 24 around the stoma receiving apertures. However, a peelable seal remains between the peripheral edges of the outer pouch walls 2a and 2b to allow such walls to be peeled apart and expose the inner pouch 3.

This embodiment has the same advantages as the FIG. 11 embodiment plus the advantage that the inner pouch 3 can be separated from the outer pouch 2 more easily and with less risk of rupturing the inner pouch during the separation.

Figure 15:
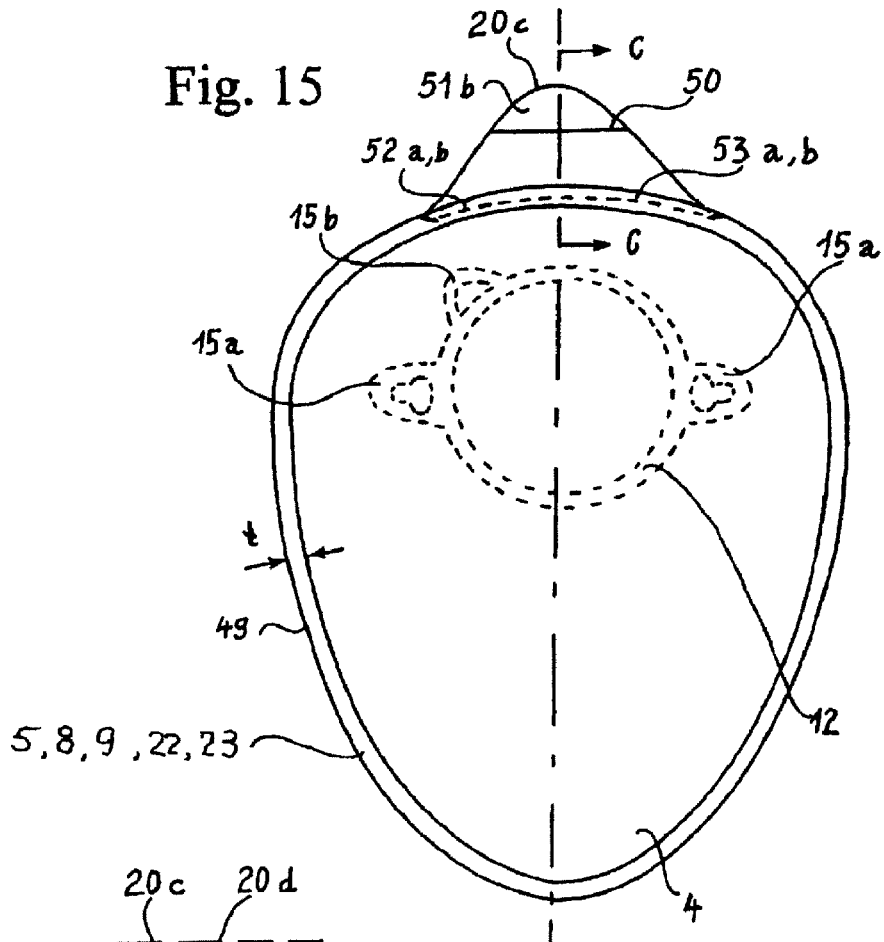
FIG. 15 is a schematic plan view, seen from the distal side, of the currently preferred embodiment of a two-piece ostomy pouch according to the invention.
Figure 16:
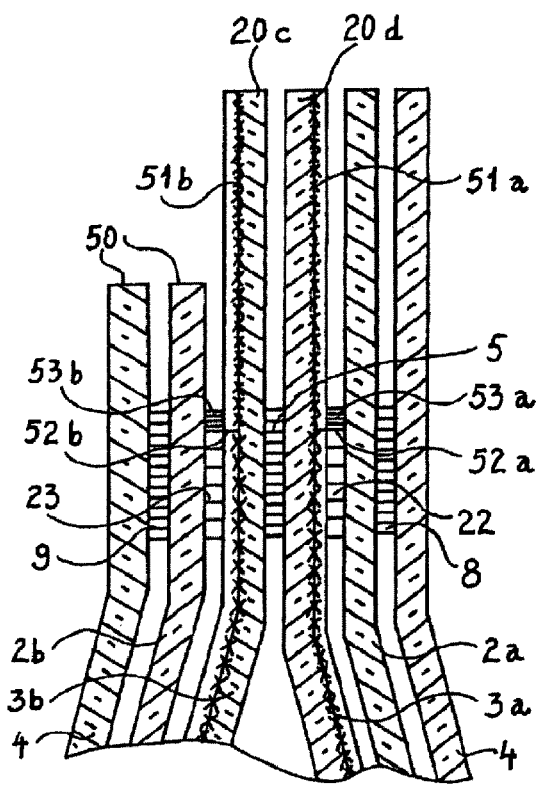
FIG. 16 is a diagrammatic cross sectional enlarged scale view taken along line C-C in FIG. 15 with the film thicknesses exaggerated for illustrative purposes.

Referring now to FIGS. 15 and 16, this currently preferred embodiment is similar to the embodiment shown in FIGS. 4-5. The inner and outer pouches 3 and 2 are symmetrical about a vertical axis of symmetry.

The paper sheet or any other suitable fibrous layer adhered or laminated to the outer surfaces of the inner pouch walls 3a and 3b may wick water present at the peripheral edge of the pouches 2 and 3, for instance when the user of the pouch assembly is bathing or showering, into the peelable seals 22 and 23 whereby the sealing strength thereof may be reduced to an extent that the seals 22 and 23 fail whereby the outer pouch walls 2a and 2b may become unintentionally separated from the inner pouch walls 3a and 3b.

To prevent this wicking from taking place, the outermost portion of the peripheral sealing seams 5, 8, 9, 22 and 23 is cut away along line 49 such that the heat generated by the cutting action melts and fuses the plastic material of outer and inner pouch walls 2a, 2b and 3a, 3b to create a seal along line 49 preventing water from coming into contact with the fibrous layers on the outer surfaces of the inner pouch walls 3a and 3b and thus preventing the wicking of water into the peelable seals 22 and 23.

The distal cover sheet 4 and the distal outer pouch wall 2b are cut away along cut lines 50 to expose a region 51b of the upper tab portion of the distal inner pouch wall 3b such that when initiating the peeling off of the outer pouch wall 2b with corresponding cover sheet 4, the user of the pouch assembly or a caregiver can grip the inner pouch tabs projecting above the cut lines 50 with one hand and grip the shortened tab portions below the cut lines 50 with the other hand and peel downwards in a manner very similar to the manner illustrated in FIG. 13.

So as to avoid wicking of water into the peelable seals 22 and 23 through the fibrous material attached to the outer surfaces of the tab portions 20c and 20d of the inner pouch walls 3b and 3a, respectively, heat is applied to areas 51a and 51b of the tab portions 20d and 20c, respectively, delimited by the peripheral edge of the tab portions and the dotted lines 52a and 52b, respectively, so as to melt the film material of the inner pouch walls in these areas so that the film material penetrates between the fibers of the fibrous material thereby reducing the wicking ability of the fibrous material.

As the areas 51b and 51a of the inner pouch tabs extend into the area of the peelable seams 22 and 23 thereby forming the areas 53a and 53b defined by the dotted lines 52a and 52b, these areas 53a and 53b are subjected to the heat sealing applied to form the peelable seals 22 and 23 whereby the wicking ability of the fibrous material is completely eliminated in the areas 53a and 53b because of further melting of the inner pouch wall film and melting of the outer pouch wall film whereby the interstices between the fibers in the fibrous material are substantially blocked and consequently no wicking path can be established for water inflow into the peelable seals 22 and 23.

It has turned out that for obtaining the best peel results the width of the peelable seals 22 and 23 should be between 4 and 6 mm, preferably approximately 5 mm, and that the width of the region in which heat and pressure is applied to form the peelable seal should be about 2 mm larger so that approx. 2 mm of the initial width of the peelable seals 22 and 23 is removed by the anti wicking cut along line 49.

Because of the symmetrical shape of the inner and outer pouches, the peeling action to peel off the distal outer pouch wall and the inner pouch takes place substantially parallel to the axis of symmetry and has turned out to require the least dexterity and force application to carry out the peeling action.

If the fibrous material attached to the outer surfaces of the inner pouch walls 3a and 3b is paper with a certain orientation of the cellulosic fibers, it has turned out that the orientation of the cellulosic fibers should be transverse to the peeling direction, i.e. in the case of the embodiment in FIGS. 15 and 16, transverse to the axis of symmetry, preferably substantially orthogonal to said axis. Hereby the best peeling result is obtained where most of the paper layer remains attached to the inner pouch walls after peeling of the peelable seams 22 and 23 has taken place.

All the features discussed in connection with the two-piece embodiments may be applied to the one-piece embodiments, and vice versa.

Furthermore, the insert 27 of FIG. 7, the triple tongues 30-32 of FIGS. 9 and 10, the paper/film laminate of the inner pouch walls of FIGS. 2, 5, 11 and 12, the double adhesive annular film 26 of FIGS. 7 and 9, the contours with pointed ends 33 and 34 and 36 and 37 of the sealing seams 6, 7 and 35, respectively, and the anti-wicking measures, the peeling seam width and the paper fiber orientation of FIGS. 15 and 16, may all be applied to the rest of the embodiments shown and described.

The polyester or copolyester film material of an ostomy pouch or fecal incontinence pouch embodying this invention is obtained by chemical synthesis rather than by a fermentation process. Polyester or copolyester films produced by a fermentation process are considered unsuitable because they tend to be brittle and cannot be converted into thin flexible films. Examples of synthetic biodegradable polyesters are aliphatic polyesters such as polycaprolactone ("Tone" from Dow Chemical) and aliphatic-aromatic copolyesters with less than 20% by mole of aromatic diacid component ("Estar Bio" from Eastman Chemical, "Ecoflex" from BASF). A synthetic biodegradable polyester precompounded with biodegradable plasticizers and suitable for thin film extrusion is available commercially from Petroplast Vinora under the designation "KF02B".

Figure 17:
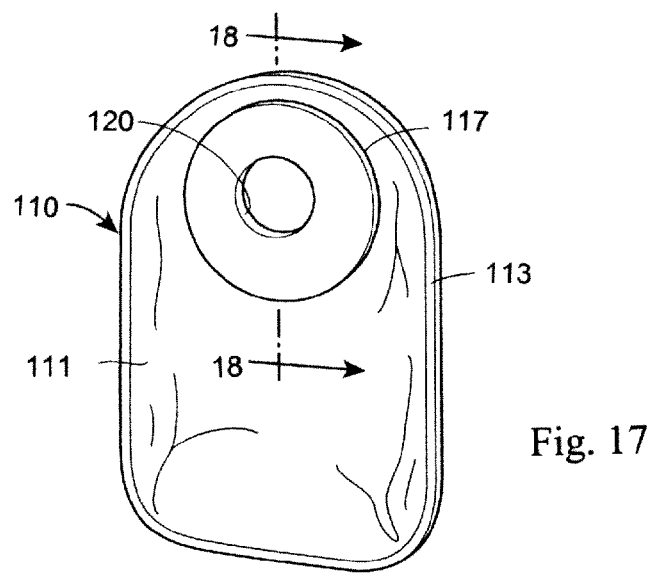
FIG. 17 is an elevational view of a flushable body waste collection pouch embodying the invention.
Figure 18:
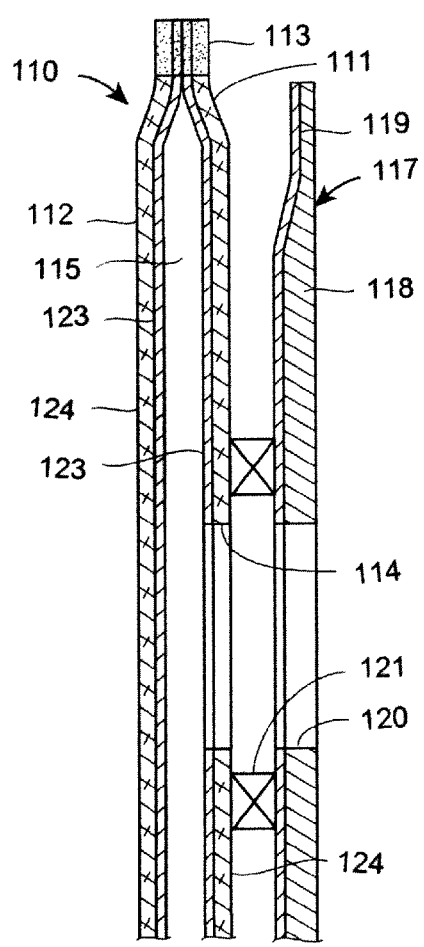
FIG. 18 is a somewhat-schematic vertical sectional view taken along line 18-18 of FIG. 17.

Referring to FIGS. 17 and 18 of the drawings, the numeral 110 generally designates a toilet-flushable body waste collection pouch with proximal (rear or bodyside) and distal (front) walls 111 and 112 having their peripheral edges joined together along a heat seal zone 113. For purposes of illustration, an ostomy pouch is shown, but the invention is applicable to other body waste collection pouches such as fecal incontinence pouches. Also, the terms "heat seal" and "heat sealing" should here be understood to include other forms of thermoplastic welding such as RF sealing. As shown, the proximal or bodyside wall is provided with an opening 114 communicating with the chamber 115 of the pouch.

The appliance 110 includes a faceplate 117 having a soft, pliant adhesive layer 118 for adhesive attachment to the peristomal skin surfaces of a wearer. A cover film 119 extends over the pouch-facing surfaces of the faceplate's adhesive layer 118, and a stoma-receiving opening 120 is provided in the faceplate in alignment with the opening 114 in the pouch. Attachment means 121 is schematically illustrated in FIG. 18 for joining the faceplate and pouch together. Such attachment means may take the form of a releasable mechanical coupling or a separable adhesive seal, all as well known in the art. For purposes of this embodiment of the invention, which focuses on pouch 110 and the materials from which it is formed (and the combination of that pouch with an outer pouch 110'), the attachment 121 is critical only to the extent that there must be some means around the stoma-receiving opening 114 for securing the pouch to a wearer.

Pouch 110 has its walls 111 and 112 formed of an ultra-thin heat-sealable (including RF sealable) liquid and gas impermeable film 123 externally bonded to a thin water-disintegratable cover layer 124. As previously stated, the film 123 is of a composition comprising a biodegradable, thermoplastic and heat-sealable, aliphatic polyester, or aliphatic-aromatic copolyester, or blends thereof, combined with a biodegradable plasticizer or combination of such plasticizers. The soft, flexible, water disintegratable cover layer 124 is composed of a random arrangement of water-dispersible non-thermoplastic fibers, preferably cellulosic fibers, and has significant tensile strength when dry but lacks such strength when wet, all as already described. The two layers are mechanically bonded together, preferably by heat, in such a way that despite the ultra-thin character of the film and the fibrous nature of the cover layer, there is no significant penetration of the fibers into the film and no formation of pinholes through the film. While some very limited penetration of the fibers into the film may exist to produce the weak mechanical bond between the layers, the penetration is so slight and the bonding forces so weak that the two layers (when dry) may be easily peeled apart with each layer remaining intact during and following such a peeling operation. More specifically, the mechanical attachment between the film and cover layer must be sufficiently weak to allow separation by the application of a 180 degree peeling force of about 2 to 10 g/in (0.02 to 0.1 Newtons/in), preferably about 3 to 6 g/in (0.03 to 0.06 Newtons/in), when tested in accordance with TAPPI Test Method UM502 (1991), all with little or no evidence of fiber retention by the film. Under such circumstances, the separated film will be free of pinholes that might otherwise cause fluid (liquid) leakage of the laminated two-layer product in use.

Figure 19:
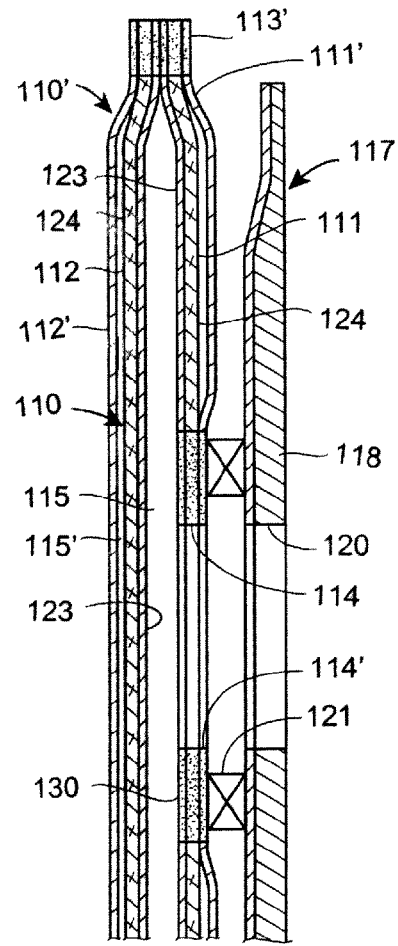
FIG. 19 is a sectional view similar to FIG. 18 but showing the flushable pouch as the inner pouch of a pouch-in-pouch appliance.

The water-disintegratable cover layer of non-thermoplastic water-dispersible fibers also plays an important role when the pouch serves as the inner pouch of a two-pouch (pouch-in-pouch) appliance as shown in FIG. 19. As there shown, pouch 110 is disposed within the chamber 115' of an outer pouch 110'. The peripheral edge portions of the two pouches may be joined together by heat sealing 113' which should be understood here to include RF sealing. The outer pouch 110' is of conventional construction and composed of any of a variety of known thermoplastic film materials that have a sufficiently high heat sealing or melting temperature and that are impermeable to liquids, gases and odors. It includes a proximal (rear or bodyside) wall 111' and a distal (front) wall 112' with the proximal wall having a stoma-receiving opening 114' aligned with the corresponding opening 114 of the inner pouch. The two pouches are sealed together, as by heat seal 130, about their respective openings. Therefore, body waste passing into the appliance can only enter the inner pouch and not the space between the two pouches.

As brought out in U.S. patent application Ser. No. 10/969, 523, published as US 2005/0113770, the disclosure of which is incorporated by reference herein, the peripheral seal 113' and the seal 130 about stoma openings 114, 114' are peelable seals that allow the proximal and distal walls 111' and 112' of the outer pouch to be peeled away from the inner pouch without disrupting the integrity of the peripheral seal that holds the walls of the inner pouch together. Thus, the walls of the outer pouch may be peeled away to expose the biodegradable inner pouch 110 so that the latter may be discarded along with its contents into a flush toilet. The outer pouch 110', which may or may not be biodegradable, may then be placed into any suitable waste receptacle.

As already noted, the fibrous and porous water-disintegratable layer 124 and the film layer 123 that together form the walls of the inner pouch have their major surfaces areas only weakly bonded together, allowing them to be separated intact from each other with the application of only limited peeling force. However, that does not include the peripheral heat seal zone 113' of the pouch shown in FIG. 19, where the film layers 123 of the inner pouch are securely heat sealed or welded to each other and also penetrate the pores of the peripheral zones of the fibrous layers 124 to produce a secure bond with the fibrous layers along the periphery of the inner pouch. The peripheral zones of the fibrous layers are also penetrated to at least some extent by the heat sealable material forming the walls 111' and 112' of the outer pouch 110'. However, the strength of the bond in the peripheral zones between the fibrous layers and the films of the inner pouch is much greater than between the fibrous layers and the thermoplastic films forming the walls of the outer pouch because the melting temperature of the inner pouch film material is substantially lower than the melting temperature of the outer pouch film material. The result is that when a user peels away the walls of the outer pouch to expose the inner pouch, the water-disintegratable, non-heat-sealable tissue paper layers of the inner pouch remain as part of the inner pouch and are not stripped away with the walls of the outer pouch.

Differential scanning calorimetry (DSC) can be used to measure the melting point of candidate film materials and to predict if a certain combination of films might be suitable for the inner and outer pouches. For example, it has been found that a biodegradable plasticized polyester available from Petroplast Vinora under the designation KF02B has a DSC melting peak of 65 degrees C. A known multilayer barrier film currently used commercially for ostomy pouches has a heat-sealable skin layer of poly(ethylene vinylacetate) (EVA) with a DSC melting peak of 88 degrees C. Because of this difference in melting temperatures, it is possible to control heat sealing conditions so that the tissue layer in the peripheral areas of the pouch walls exhibits a stronger bond with the inner pouch film than with the outer pouch film following a heat sealing operation (including RF sealing). As a result, the outer pouch can be peeled away without causing separation of the tissue layer from the inner pouch film. A melting temperature differential of at least 10 degrees C. is believed to be needed to control layer separation.

To facilitate the step of manually peeling away the proximal and distal walls of outer pouch 110', such walls may be provided with gripping tabs (not shown) that project outwardly beyond the peripheral edges of inner pouch 110.

The walls of the inner pouch must be impermeable to fluid and solid body wastes, and the biodegradable plasticized polyesters or copolyesters described herein perform that function well. Biodegradable polyesters or copolyesters, while generally considered gas impermeable, nevertheless allow diffusion of odors to an extent that renders them, without some protective means, unsuitable for body waste collection pouches intended for more than extremely short durations of use. A plasticized biodegradable polyester or copolyester pouch in the condition shown in FIGS. 17 and 18 is therefore useful for periods substantially shorter than one hour as, for example, as a pouch to be used with stomal implants where the duration of use may be 30 minutes or less. Despite the odor permeability of such biodegradable polyester materials, however, pouches formed therefrom are well suited for long term body waste collection if they are used for the inner pouches of two pouch systems, as shown in FIG. 19, with odor impermeability then provided by the protective outer pouches. Any of a variety of well-known heat-sealable pouch materials that are odor impermeable are suitable for fabrication of outer pouch 110' which is not intended to be toilet flushable.

As described above, cover layer 124 of inner pouch 110 is of a porous material that is supportive when dry but has low wet strength. It should also be soft and flexible. Tissue paper that has a high percentage (preferably 100%) of cellulosic fibers is preferred such as, for example, a cellulosic tissue paper of the type available from Shawano Specialty Papers having a basis weight of 14 lb/ream. Absence of a binder is desirable because a binder may interfere with or retard the rate of disintegration, but a limited amount of a binder that is non-thermoplastic and readily soluble or disintegratable in water, such as starch, may be acceptable. The porous tissue layer for each wall 111 and 112, when such layer is in a dry state, provides reinforcement, softness, and noise reduction for the thin thermoplastic film of the inner pouch and is believed to contribute to the flushability of the film when the inner pouch is separated from the outer pouch and discarded into a flush toilet.

As believed evident from the above, the method of making a pouch-in-pouch waste collection appliance embodying this invention involves the steps of selecting a thermoplastic material for the film of the inner pouch that has a melting temperature substantially lower than that of the thermoplastic material for the film of the outer pouch and then joining together peripheral portions of the walls of the two pouches by simultaneously applying pressure and heat so that the film material of the inner pouch melts and invades the pores of the fibrous cover layer to a greater extent than the film material of the outer pouch. At the same time, the opposing or inwardly-facing film layers of the inner pouch become fused to each other, forming a true heat seal or weld between the walls of the inner pouch. Upon the subsequent application of peeling forces, the walls of the outer pouch may then be peeled away from those of the inner pouch without causing separation of the porous cover layer and film layer of the inner pouch and without disrupting the integrity of the inner pouch. The exposed inner pouch and its contents are then discarded into a flush toilet.

It will be noted from FIG. 19 that the proximal wall of the outer pouch may be similarly joined to the porous cover layer of the proximal wall of the inner pouch around the stoma-receiving opening so that as the proximal wall of the outer pouch is peeled away from the proximal wall of the inner pouch, that is, when the inner pouch is extracted from what remains of the cavity of the outer pouch, a clean separation will occur with the porous cover layer again being retained as part of the flushable inner pouch.

Other features and advantages of the invention will become apparent from the following examples:

Example 1

Two methods are particularly suitable for the production of the tissue/film laminate of pouch 10: (1) extrusion coating onto tissue paper (1 step), and (2) film extrusion followed by lamination of the film to tissue paper (2 steps). Extrusion coating may be accomplished using a Davis Standard extrusion coating line. Tissue paper is used as a substrate and the biodegradable polyester is directly extruded onto the tissue in a single step process. With a two-step process, film may be first extruded using a blown film extrusion line and then laminated to paper tissue paper using a Faustel laminator. Lamination is ideally accomplished thermally with no adhesive layer between tissue and film. Both processes (1) and (2) give high quality laminates with no wrinkles or other defects. A two-step process is preferred because it affords better control of the adhesion and interpenetration between tissue and film. A temperature in the 165° to 220° F. range and a nip pressure in the 40-50 psi range are typically used for lamination. It is from such a laminate that the walls of the pouch may then be die-cut.

Example 2

Blends of polycaprolactone ("Tone 787" from Dow Chemical) and triethylcitrate ("Citroflex 2" from Morflex Corp.) were compounded and pelletized using a twin-screw compounder extruder. The compounded pellets were converted into film using a cast film line equipped with a 1.25 inch extruder having an L/D ratio of 24:1. Film was extruded at a die temperature of 320° F. The following table illustrates the effect of plasticizer content on tensile modulus and noise at a film thickness of 0.6 mil (15.2 microns):

| Effect of Triethylcitrate Content (TEC) on Tensile Modulus and Noise of Polycaprolactone (PCL) | | | |
|---|---|---|---|
| | PCL Unplasticized | PCL, 10% TEC | PCL, 20% TEC |
| Tensile modulus, psi(*) | 48200 | 25600 | 9950 |
| Noise(**) | | | |
| dBA | 69 | 65 | 55 |
| dB. 8 kHz | 56 | 51 | 41 |

(*)Secant modulus at 2% elongation, ASTM D882 (initial strain rate: 10 in/in min)
(**)Film sample is formed into a cylinder and mounted on a test fixture wherein one end is held fixed and the other is rotated around the cylinder axis (15 degree angle, 70 cycles/min). Noise emissions from film flexing are analyzed with a sound level meter. dBA is a weighted average which takes into account the human perception of noise over the entire frequency range, dB in the 8 kHz octave band is indicative of the noise in the high frequency range and represents the crispness of the noise.

The data in this table shows that increasing triethylcitrate plasticizer content reduces the modulus of the polycaprolactone film (i.e., increases its flexibility) and reduces the noise of the film. At 20% TEC, however, film blocking, (where the surfaces of adjacent films stick together) becomes a problem. A plasticizer level of 10% is preferred because it provides adequate flexibility and quietness without blocking.

Example 3

As ostomy pouch suitable for use as the inner pouch of a two-pouch appliance was constructed with a thin, plasticized polycaprolactone film of 0.2 to 0.6 mil (5.1 to 15.2 microns) prepared in accordance with Example 2. The pouch was found to flush well even with a low-volume toilet system (1.6 gal).

Example 4

Another biodegradable film suitable for fabricating flushable ostomy pouches was formed by heat-lamination of a plasticized biodegradable synthetic polyester film having a thickness within the range of 0.4 to 0.8 mil (10.2 to 20.3 microns) identified as "KF02B" from Petroplast Vinora, Switzerland to a 100% cellulosic tissue having a basis weight of 14 lb/ream (product code no. 3040 from Shawano Specialty Papers).

Example 5

The improved biodegradability of a polyester film blended with a biodegradable plasticizer is illustrated by this example.

Biodegradability was tested on film samples consisting of (1) polycaprolactone ("Tone 787" PCL from Dow Chemical)

plasticized with triethylcitrate (PCL/TEC weight ratio of 90/10), (2) unplasticized PCL ("Tone 787" from Dow Chemical) and (3) a control sample of polyvinylalcohol film taken from a commercially available flushable inner pouch product ("Impact" flushable ostomy bag from Welland Medical Limited, Crawley, England). The films were exposed to aerobic sewage sludge inoculum in accordance with ASTM test method D-5209. The average weight losses were (1) 64.0%, for the plasticized PCL, (2) 26.1% for the unplasticized PCL, and (3) 12.4% for the control sample.

The plasticized PCL therefore exhibited higher weight loss due to biodegradation than the unplasticized PCL and much higher loss than the commercial PVOH inner pouch material claimed by the manufacturer to be biodegradable.

Example 6

This example illustrates the conditions required to laminate a tissue paper to a thin biodegradable film without causing pinhole formation in the process.

A biodegradable film from Petroplast Vinora (KF02B, 20 microns thick) and a cellulosic tissue from Shawano Specialty Papers (Product Code 3040, basis weight 14 lb/ream) were heat laminated using a Faustel laminator. The nip pressure was 50 psi, the temperature 220 degrees F., and the line speed 35 to 40 feet per minute. The laminate exhibited a 180 degree peel strength in the 3-6 g/in range.

The laminate was tested for pinholes as follows: A sample of the laminate was laid on a flat surface with the film side facing up. A blue dye solution was applied on the surface of the film. After 5 minutes the film was turned over and the tissue side inspected. If pinholes were present, the dye solution would have wicked into the tissue producing visible blue dots. The test showed no evidence of pinholes. As the laminator line speed was decreased or the nip pressure increased, the peel strength became progressively higher with evidence of residual fibers embedded in the film and pinholes appeared in the dye wicking test.

Example 7

This example illustrates the resistance to deformation imparted by tissue lamination to a thin biodegradable film.

The load at 1% and 2% strain was measured in accordance with ASTM D882-02 for the film-tissue laminate of Example 6 and for the film of Example 6 without tissue. Results are illustrated in the following table:

|  | Load @ 1% strain, MD (*) lb/in | Load @ 2% strain, MD (*) lb/in | Load @ 1% strain, TD () lb/in | Load @ 2% strain, TD () lb/in |
| --- | --- | --- | --- | --- |
| Laminate of Example 6 | 0.84 | 1.48 | 0.83 | 1.35 |
| Film of Example 6 (no tissue) | 0.35 | 0.62 | 0.54 | 0.90 |

(*) MD: machine direction
(**) TD: transverse direction

Example 8

This example illustrates differences in heat sealing properties of films suitable for use in pouch-in-pouch appliances embodying the invention. Materials suitable for the walls of the inner pouch are heat-sealable biodegradable films of 20 microns thickness of plasticized polyester from Petroplast Vinora (KBF02B). A thermoplastic material suitable for the walls of the outer pouch is a commercial multilayer barrier film for ostomy pouches having a heat-sealable skin layer of EVA. In each test, two layers of the same film material were heat sealed together, or sought to be heat sealed together, for an interval of 1.2 seconds with a sealing element maintained at different selected temperatures and at a sealing pressure of 4 bar. Following cooling the strength of the seal (if any) was tested by manually peeling apart, or attempting to peel apart, the two layers. The results of such tests are given below:

|  | Sealing Behavior/Observation | |
| --- | --- | --- |
| Temperature | 75 Micron Commercial Barrier Film with EVA Skin Layer | 20 Micron KF02B |
| 80° C. | — | No Bonding |
| 90° C. | — | Peel |
| 100° C. | — | Peel |
| 110° C. | — | Peel |
| 120° C. | No Bonding | Peel |
| 130° C. | No Bonding | Peel |
| 135° C. | Peel | Full Seal |
| 140° C. | Peel | — |
| 150° C. | Peel | — |
| 160° C. | Peel | — |
| 170° C. | Full Seal | — |

The term "Peel" as used in the chart means that the two layers had limited adherence to each other but could nevertheless be separated or peeled apart with each layer remaining intact. "Full Seal" means that the layers had become welded or fused together and could not be so separated. The chart reveals that the KFO2B film had significantly lower heat sealing temperatures than the control film. This is consistent with the DSC melting temperatures discussed earlier.

While in the foregoing we disclosed embodiments in considerable detail for purposes of illustration, it will be understood by those skilled in the art that many of such details may be varied without departing from the spirit and scope of the invention.

The invention claimed is:

1. A biodegradable body waste collection pouch particularly suitable for flush toilet disposability; said pouch having a pair of walls secured together along their peripheral edges to define a waste-receiving chamber therebetween; one of said side walls having a waste-receiving opening therethrough communicating with said chamber; and external attachment means provided about said opening for attachment of said pouch to a wearer; said walls of said pouch being cut from a laminate comprising (a) a layer of thin heat-sealable film impermeable to liquid and solid body wastes and of a composition comprising a biodegradable aliphatic polyester, or a biodegradable aliphatic-aromatic copolyester, or blends thereof, plasticized by one or more biodegradable plasticizers and (b) a water-disintegratable biodegradable cover layer of water-dispersible fibers having one of its surfaces uninterruptedly bonded thereto; said water-dispersible fibers along at least a portion of the outer surface of said pouch being coated with a water-soluble hydrophilic lubricating agent, said hydrophilic lubricating agent coated on said water-dispersible fibers being capable of becoming slippery when exposed to water and, upon subsequent drying, again becoming water-soluble upon re-exposure to water.

2. The collection pouch of claim 1 in which said hydrophilic lubricating agent is selected from the group consisting of hydroxyethylcellulose, hydroxypropylcellulose, carboxymethylcellulose and their salts, polyethylene glycol, gums, gelatin, pectin, polyethyleneoxide, polyacrylamides, acrylic acid copolymers and their salts, and water-soluble silicone lubricating agents.

3. The collection pouch of claim 1 in which said hydrophilic lubricating agent is dry but, when said pouch is immersed in water in a flush toilet for a period less than 60 seconds, becomes hydrated and slippery, so as to promote flushability of the pouch and facilitate its passage through a sanitary sewer system.

4. The collection pouch of claim 1 in which the thickness of said film is no greater than about 40 microns.

5. The collection pouch of claim 1 in which said layers of said laminate are weakly bonded together and may be separated from each other with each layer remaining intact by the application of 180-degree peeling forces in the range of about 2 to 10 g/in.

6. The collection pouch of claim 1 in which said composition comprises a blend of about 70% to 95% by weight of said biodegradable aliphatic polyester or aliphatic-aromatic copolyester, and about 5% to 30% by weight of one or more of said biodegradable plasticizer or plasticizers.

7. The collection pouch of claim 1 in which said aliphatic polyester or the aliphatic component of said copolyester comprises a polymer formed by ring-opening polymerization of a lactone.

8. The collection pouch of claim 1 in which said aliphatic-aromatic copolymer comprises a condensation product of a glycol with a combination of an aliphatic diacid and an aromatic diacid, wherein the aromatic diacid is less than 20% by mole.

9. The collection pouch of claim 1 in which said film of a biodegradable aliphatic polyester or copolyester is a monolayer.

10. The collection pouch of claim 1 in which said fibers of said water-disintegratable cover layer are cellulosic.

11. The collection pouch of claim 10 in which said cover layer comprises tissue paper formed of 100% cellulosic fibers.

12. The collection pouch of claim 1 in which said cover layer is heat-bonded to said film.

13. A method of promoting the flushability of a waste collection pouch in a flush toilet, comprising the steps of providing a pouch with a pair of walls secured together along their peripheral edges to define a waste-receiving chamber therebetween; one of said walls having a waste-receiving opening therethrough communicating with said chamber; said walls being formed from a laminate comprising (a) a layer of thin heat-sealable film impermeable to liquid and solid body wastes and of a composition comprising a biodegradable aliphatic polyester, or a biodegradable aliphatic-aromatic copolyester, or blends thereof, plasticized by one or more biodegradable plasticizers, and (b) a water-disintegratable biodegradable cover layer of water-dispersible fibers having one of its surfaces uninterruptedly bonded thereto, comprising the step of coating said water-dispersible fibers along at least a portion of the outer surface of said laminate, either before or after assembly of said pouch, with a water-soluble hydrophilic lubricating agent, said hydrophilic lubricating agent coated on said water-dispersible fibers being capable of becoming slippery when the outer surfaces of said pouch are exposed to water and, upon subsequent drying, again become water-soluble upon re-exposure to water, said step of coating said water-dispersible fibers with said hydrophilic lubricating agent comprising applying a water-based hydrophilic solution to said water-dispersible fibers, said water-based hydrophilic solution comprising said hydrophilic lubricating agent.

14. The method of claim 13 in which said hydrophilic lubricating agent is selected from the group consisting of hydroxyethylcellulose, hydroxypropylcellulose, carboxymethylcellulose and their salts, polyethylene glycol, gums, gelatin, pectin, polyethyleneoxide, polyacrylamides, acrylic acid copolymers and their salts, and water-soluble silicone gelling agents.

15. The method of claim 13 in which said hydrophilic lubricating agent is in the form of a dry coating but, when said pouch is exposed to water in a flush toilet for a period less than 60 seconds, becomes hydrated and slippery, so as to promote flushability of the pouch and facilitate its passage through a sanitary sewer system.

16. The method of claim 13 in which said step of coating said fibers along at least a portion of said outer surface with said water-soluble hydrophilic lubricating agent occurs immediately prior to discarding said pouch and its contents into a flush toilet.

17. A pouch-in-pouch body waste collection appliance comprising an outer pouch formed of liquid, gas and odor impermeable heat-sealable polymeric film having proximal and distal side walls defining a chamber; a toilet-disposable inner pouch having proximal and distal side walls and being disposed in said chamber; said proximal walls of said inner and outer pouches having aligned body waste receiving openings therethrough; and attachment means for attaching said proximal walls of said inner and outer pouches in areas surrounding said openings to skin surfaces of a patient about a body waste discharge orifice; said disposable inner pouch having walls formed from sheet material comprising (a) a layer of thin heat-sealable film impermeable to body wastes of a composition comprising a biodegradable aliphatic polyester, or a biodegradable aliphatic-aromatic copolyester, or blends thereof, plasticized by one or more biodegradable plasticizers and (b) a water-disintegratable, porous, biodegradable cover layer of water-dispersible fibers bonded thereto; said heat-sealable film of said inner pouch having a melting temperature lower than that of the heat-sealable film of said outer pouch; said walls of said outer and inner pouches having peripheral edge portions heat-sealed together with the peripheral edge portions of said cover layer being bonded more securely to the film material of said inner pouch than to the film material of said outer pouch; said water-dispersible fibers along at least a portion of the outer surface of the walls of said inner pouch being coated with a water-soluble hydrophilic lubricating agent, said hydrophilic lubricating agent coated on said water-dispersible fibers being capable of becoming slippery when exposed to water and, upon subsequent drying, again becoming water-soluble upon re-exposure to water.

18. The collection appliance of claim 17 in which said hydrophilic lubricating agent is selected from the group consisting of hydroxyethylcellulose, hydroxypropylcellulose, carboxymethylcellulose and their salts, polyethylene glycol, gums, gelatin, pectin, polyethyleneoxide, polyacrylamides, acrylic acid copolymers and their salts, and water-soluble silicone gelling agents.

19. The collection appliance of claim 17 in which said hydrophilic lubricating agent is in the form of a dry coating on fibers of said cover layer but, when said inner pouch is immersed in water in a flush toilet for a period less than 60 seconds, becomes hydrated and slippery, so as to promote flushability of said inner pouch and facilitate its passage though a sanitary sewer system.

20. A method of making a pouch-in-pouch body waste collection appliance having an outer pouch formed of odor-impermeable thermoplastic film with proximal and distal walls defining a chamber and a toilet-disposable inner pouch having proximal and distal walls and being disposed in said chamber; said proximal walls of said inner and outer pouches having aligned body waste receiving openings therein; said walls of said inner pouch being formed of a laminate comprising (a) a layer of thin heat-sealable thermoplastic film, and (b) a porous water-disintegratable cover layer of water-dispersible fibers attached to exterior surfaces of said inner pouch film, said cover layer having at least some of said water-dispersible fibers along the exterior surface of said inner pouch coated with a water-soluble hydrophilic lubricating agent, said hydrophilic lubricating agent coated on said water-dispersible fibers being capable of becoming slippery when exposed to water and, upon subsequent drying, again becoming water-soluble upon re-exposure to water; wherein said method comprises the steps of selecting a material for the film of an inner pouch having a melting temperature substantially lower than that of the material of said outer pouch; coating said water-dispersible fibers along at least a portion of the outer surface of said laminate, either before or after assembly of said pouch, with a water-soluble hydrophilic lubricating agent, said step of coating said water-dispersible fibers with said hydrophilic lubricating agent comprising applying a water-based hydrophilic solution to said water-dispersible fibers, said water-based hydrophilic solution comprising said hydrophilic lubricating agent; and joining together peripheral portions of said walls of said inner and outer pouches, and portions of said proximal walls of said inner and outer pouches surrounding said body waste receiving openings, by simultaneously applying pressure and heat to said portions so that said proximal and distal walls of said inner pouch are welded together and, simultaneously, said film material of said inner pouch melts and invades the pores of said fibrous cover layer to a greater extent than said film material of said outer pouch, where, upon the subsequent application of peeling forces, said walls of said outer pouch may be peeled away from said inner pouch without causing separation of said cover and film layers of said inner pouch.

21. The method of claim 20 in which said fibers along the peripheral portion of said inner pouch joined to said peripheral portion of said outer pouch are coated with said water-soluble hydrophilic lubricating agent.

22. The method of claim 20 in which said fibers along the peripheral portion of said inner pouch joined to said peripheral portion of said outer pouch are not coated by said water-soluble hydrophilic lubricating agent.

23. The method of claim 20 in which said film material of said inner pouch has a melting temperature at least 10° C. below the melting temperature of said outer pouch film.

24. The method of claim 20 in which said fibers of said cover layer are cellulosic or other equivalent material.

25. The method of claim 24 in which said cover layer comprises tissue paper of 100% cellulosic fibers.

26. The method of claim 20 in which said cover layer and said thermoplastic film of said inner pouch, throughout the areas between said peripheral portions and said portions surrounding said openings, are weakly bonded together and may be separated from each other with each layer remaining intact by the application of 180-degree peeling forces in the range of about 2 to 10 g/in.

27. The method of claim 20 in which said film of said inner pouch has a thickness no greater than about 40 microns.

28. An ostomy appliance for receiving discharge from a human stoma and comprising
attachment means for attaching the appliance to the peristomal skin surface of a user of the appliance,
and an ostomy assembly comprising:
an inner pouch attached to said attachment means and having a first aperture for receiving the stoma of said user, said inner pouch being defined by a flexible body side or proximal inner pouch wall and a flexible distal inner pouch wall, and one or more peripherally extending inner pouch sealing seams,
an outer pouch enclosing said inner pouch, attached to said attachment means and having a second aperture for receiving said stoma and being aligned with said first aperture, said outer pouch being defined by a flexible bodyside or proximal outer pouch wall and a flexible distal outer pouch wall, and one or more peripherally extending outer pouch sealing seams,
said one or more outer pouch sealing seams being manually peelable such that the attachment forces provided by said one or more peelable outer pouch sealing seams may be manually eliminated by manually pulling said distal outer pouch wall in a direction transverse to said one or more peelable outer pouch sealing seams,
said inner pouch walls being made of a plastic film laminated to a web of a non-woven fibrous material, said web facing outwards relative to the interior of said pouch and having an externally exposed coating of a water-soluble hydrophilic lubricating agent, said hydrophilic lubricating agent coated on said web being capable of becoming slippery when exposed to water and, upon subsequent drying, again becoming water-soluble and slippery upon re-exposure to water.

29. An ostomy appliance of claim 28 wherein at least one of said non-woven material and said plastic film is biodegradable.

30. An ostomy appliance of claim 28 wherein said inner pouch walls are impermeable to liquid and gas and permeable to odors, and said outer pouch walls are impermeable to liquid, gas and odors.

31. An ostomy appliance of claim 30 wherein said one or more outer pouch peeling seams comprises a peeling action initiation zone, where said one or more outer pouch sealing seams comprises a peak-like extent tapering in the direction opposite a predetermined peeling direction.

32. An ostomy appliance of claim 28 wherein said one or more outer pouch peeling seams comprises a peeling action ending zone, where said one or more outer pouch sealing seams comprises a peak-like extent tapering in a predetermined peeling direction.

33. An ostomy appliance according to claim 32 wherein said proximal outer pouch wall is attached to said attachment means by a heat sealed sealing seam.

34. An ostomy appliance according to claim 28 wherein said hydrophilic lubricating agent is selected from the group consisting of hydroxyethylcellulose, hydroxypropylcellulose, carboxymethylcellulose and their salts, gums, gelatin, pectin, polyethylene glycol, polyethylene oxide, polyacrylamides, acrylic acid copolymers and their salts, and water-soluble silicone gelling agents.

35. An ostomy appliance according to claim 28 wherein said hydrophilic lubricating agent is dry but, when said inner pouch is immersed in water in a flush toilet for a period less than 60 seconds, becomes hydrated and slippery, so as to promote flushability of the inner pouch and facilitate its passage though a sanitary sewer system.

36. A pouch-in-pouch body waste collection appliance comprising an outer pouch formed of liquid, gas and odor impermeable heat-sealable polymeric film having proximal and distal side walls defining a chamber; a toilet-disposable inner pouch having proximal and distal side walls and being disposed in said chamber; said proximal walls of said inner and outer pouches having aligned body waste receiving openings therethrough; and attachment means for attaching said proximal walls of said inner and outer pouches in areas surrounding said openings to skin surfaces of a patient about a body waste discharge orifice; said disposable inner pouch having walls formed from sheet material comprising (a) a layer of thin heat-sealable polymeric film impermeable to body wastes and (b) a water-disintegratable, porous, biodegradable cover layer of water-dispersible fibers bonded thereto; said water-dispersible fibers along at least outer surface portions of the walls of said inner pouch being coated with a water-soluble hydrophilic lubricating agent, said hydrophilic lubricating agent coated on said water-dispersible fibers being capable of becoming slippery when exposed to water and, upon subsequent drying, again becoming water-soluble upon re-exposure to water.

37. A method for enhancing the toilet flushability of an article comprised of a thin polymeric film covered by a water-disintegratable fibrous cover layer bonded to the outer surface thereof, comprising the step of modifying said cover layer by coating at least some of said water-disintegratable fibers along the outer surface of said article with a hydrophilic agent, said hydrophilic agent coated on said water-disintegratable fibers becoming lubricious upon hydration, said step of coating said water-disintegratable fibers with said hydrophilic agent comprising applying a water-based hydrophilic solution to said water-disintegratable fibers, said water-based hydrophilic solution comprising said hydrophilic agent.

38. The method of claim 37 in which said hydrophilic agent is selected from the group consisting of hydroxyethylcellulose, hydroxypropylcellulose, carboxymethylcellulose and their salts, polyethylene glycol, gums, gelatin, pectin, polyethyleneoxide, polyacrylamides, acrylic acid copolymers and their salts, and water-soluble silicone lubricating agents.

39. The method of claim 37 in which said polymeric film is heat-sealable and impermeable to liquid and solid body wastes.

40. The method of claim of 39 in which said film comprises a biodegradable aliphatic polyester, or a biodegradable aliphatic-aromatic co-polyester, or blends thereof, plasticized by one or more biodegradable plasticizers.

41. The method of claim 37 in which thickness of said film is no greater than about 40 microns.

42. The method of claim 37 in which said cover layer is a nonwoven material formed of water-dispersible fibers.

43. The method of claim 42 in which said fibers of said water-disintegrable cover layer are cellulosic.

44. The method of claim 43 in which said cover layer comprises tissue paper formed of 100% cellulosic fibers.

45. The method of claim 37 in which said fibers coated by said hydrophilic agent are located along the outer surface of said fibrous layer cover.

46. The collection pouch of claim 2, wherein the laminate further includes one or more thickeners, preservatives odor neutralizers/deodorants, and solublization enhancers.

47. The method of claim 14, wherein the laminate further includes one or more thickeners, preservatives, odor neutralizers, deodorants, and solublization enhancers.

48. The collection appliance of claim 18, wherein the laminate further includes one or more thickeners, preservatives, odor neutralizers, deodorants, and solublization enhancers.

49. The ostomy appliance of claim 34, wherein the laminate further includes one or more thickeners, preservatives, odor neutralizer, deodorants, and solublization enhancers.

50. The method of claim 38, wherein the laminate further includes one or more thickeners, preservatives odor neutralizers/deodorants, and solublization enhancers.

51. The collection appliance of claim 18, wherein the laminate further includes one or more thickeners, preservatives, odor neutralizers, deodorants, and solublization enhancers.

* * * * *